(12) United States Patent
Inouye

(10) Patent No.: US 6,544,754 B2
(45) Date of Patent: Apr. 8, 2003

(54) OPLOPHORUS LUCIFERASE SUBUNITS

(75) Inventor: Satoshi Inouye, Yokohama (JP)

(73) Assignee: Chisso Corporation, Osaka (JP)

( * ) Notice: Subject to any disclaimer, the term of this patent is extended or adjusted under 35 U.S.C. 154(b) by 0 days.

(21) Appl. No.: 09/842,164

(22) Filed: Apr. 26, 2001

(65) Prior Publication Data

US 2002/0102687 A1 Aug. 1, 2002

(30) Foreign Application Priority Data

Apr. 26, 2000 (JP) ........................................ 2000-125053

(51) Int. Cl.$^7$ ............................. C12Q 1/66; C12N 9/02; C07K 14/435
(52) U.S. Cl. ............................. 435/8; 435/189; 530/350
(58) Field of Search ....................... 435/189, 8; 530/350

(56) References Cited

PUBLICATIONS

Inouye et al., "The use of Renilla luciferase, Oplophorus luciferase, and apoaequorin as bioluminescent reporter protein in the presence of coelenterazine analogues as substrate," Biochemical and Biophysical Research Comm., vol. 233, Apr. 17, 1997, pp. 349–353.
C. Dingwall, et al., TIBS, vol. 16, pps. 478–481, "Nuclear Targeting Sequences—A Consensus?," Dec. 1991.
Y. Gavel, et al., Protein Engineering, vol. 4, No. 1, pps. 33–37, "Cleavage–site Motifs in Mitochondrial Targeting Peptides," 1990.
Y. Gavel, et al., FEBS Letters, vol. 261, No. 2, pps. 455–458, "A Conserved Cleavage–Site Motif in Chloroplast Transit Peptides," Feb. 1990.
P. J. Herring, J. Mar. Biol. Ass. U.K., vol. 56, pps. 1029–1047, "Bioluminescence in Decapod Crustacea," 1976.
S. Inouye, et al., Analytical Biochemistry, vol. 201, pps. 114–118, "Monitoring Gene Expression in Chinese Hamster Ovary Cells Using Secreted Apoeaquorin," 1992.
S. Inouye, et al., FEBS Letters., vol. 315, No. 3, pps. 343–346, "Cloning and Sequence Analysis of cDNA for the $Ca^{2+}$–Activated Photoprotein, Cyltin," Jan. 1993.
S. Inouye, et al., Proc. Natl. Acad. Sci., vol. 89, pps. 9584–9587, "Imaging of Luciferase Secretion From Transformed Chinese Hamster Ovary Cells," Oct. 1992.
A. Kakizuka et al., Essential Developmental Biology, pps. 223–232, "cDNA Library Consruction," 1993.
R. Patnaik, et al., BioTechniques, vol. 24, No. 5, pps. 862–868, "E. coli–based in Vitro Transcription/Translation: In Vivo–Specific Synthesis Rates and High Yields in a Batch System," 1998.

J. Sambrook, et al., Molecular Cloning, A Laboratory Manual, Second Edition, pps. 12.2 to 12.44, "Screening Expression Libraries With Antibodies and Oligonucleotides," 1989.
O. Shimomura, et al., Biochemistry, vol. 17, No. 6, pps. 994–998, "Properties and Reaction Mechanism of the Bioluminescence System of the Deep–Sea Shrimp *Oplophorus gracilorostris*," 1978.
A.S. Spirin, et al., Science, vol. 242, pps. 1162–1164, "A Continuous Cell–Free Translation System Capable of Producing Polypeptides in High Yield," Nov. 25, 1988.
E.M. Thompson, et al., Proc. Natl. Acad. Sci., vol. 786, pps. 6567–6571, "Cloning and Expression of cDNA for the Luciferase From the Marine Ostracod *Vargula hilgendorfii*," Sep. 1989.
G. Von Heijne, Eur. J. Biochem., vol. 133, pps. 17–21, "Patterns of Amino Acids Near Signal–Sequence Cleavage Sites," 1983.
G. Von Heijne, et al., FEBs Letters, vol. 244, No. 2, pps. 439–446, "Species–Specific Variation in Signal Peptide Design," Feb. 1989.
R.B. Wallace, et al., Nucleic Acids Research, vol. 9, No. 4, pps. 879–894, "The Use of Synthetic Oligonucleotides as Hybridization Probes. II. Hybridization of Oligonucleotides of Mixed Sequence to Rabbit B–Globin DNA," 1981.
Inouye et al., FEBS Letters (Sep. 8, 2000), vol. 481, pp. 19–25.*
Nakamura et al. Tetrahedron Letters (Sep. 8, 1997), vol. 38, pp. 6405–6406.*

* cited by examiner

*Primary Examiner*—Elizabeth Slobodyansky
(74) *Attorney, Agent, or Firm*—Oblon, Spivak, McClelland, Maier & Neustadt, P.C.

(57) ABSTRACT

The present invention provides a polynucleotide or polynucleotides encoding Oplophorus luciferase which is composed of 19 kDa and 35 kDa proteins, or the 19 kDa photoprotein, the recombinant secretional Oplophorus luciferase or the 19 kDa photoprotein encoded by the polynucleotide(s), an expression vector containing the polynucleotide(s) and a host transformed with the vector.

Further, the invention provides a method for producing the recombinant Oplophorus luciferase or the photoprotein.

These proteins could be recombinantly produced by culturing the host cell or by in vitro translation system using the recombinant expression vector.

15 Claims, 5 Drawing Sheets

DETERMINATION OF MOLECULAR WEIGHT OF PURIFIED
*OPLOPHORUS* LUCIFERASE BY GEL FILTRATION

● : *OPLOPHORUS* LUCIFERASE a : AMYLASE (200 kDa)

b : ALCOHOL DEHYDROGENASE (150 kDa)

c : BOVINE SERUM ALBUMIN (67 kDa)

d : OVALBUMIN (43 kDa)

e : CARBONIC ANHYDRASE (30 kDa)

f : RIBONUCLEASE (13.7 kDa)

FIG. 2

ALIGNMENT OF THE LEUCINE-RICH REPEATS OF THE 35 kDa PROTEIN

RESIDUES 40-359 OF SEQ ID No: 47

| | AMINO ACID No. | SEQ ID No: |
|---|---|---|
| A V A C P A A E D I A P C T C K V G E G D V M | [40–62] | 25 |
| D M D C S K V T S D A E L A S I F S K T F P S N | [63–86] | 26 |
| T F R E L F I E F N R E I T T L T A D S L G A A | [87–110] | 27 |
| T F T K I A I T S C T Q L K T I E E N A F M A S A A | [111–136] | 28 |
| T L E K L V L L K N D L S S F P F E E M S Q Y T | [137–160] | 29 |
| K L N W L E L S V N S I T G W P A L S S D – – – | [161–181] | 30 |
| T L A N L I L F R N P I G N I P V D A F Q T L P | [182–205] | 31 |
| N I E Q F N C F D C S I T E V E A G T F T R S P | [206–229] | 32 |
| K L Q K L V L G Y N G L T S L P V G A I K L H G H G P | [230–256] | 33 |
| T T S N L G I T N N Q I I S F P E G A V E G I Q | [257–280] | 34 |
| G I – – L G I D F N R V T S L S E E V W R P I L E | [281–303] | 35 |
| N L F Q F S L L N N P L A C V C D V M W L I D S P | [304–328] | 36 |
| E L – L A K I K G N P R C A G G K R L K N L D P | [329–351] | 37 |
| A V F H A M C Q | [352–359] | 38 |

| | | SEQ ID No: |
|---|---|---|
| – L – – L – – L – – N – I – – – – P – – – – – – – – – CONSENSUS | | 40 |
| – – – – – – – – – – – L | | |

WESTERN BLOT ANALYSIS OF *OPLOPHORUS* LUCIFERASE
USING ANTI-*OPLOPHORUS* LUCIFERASE POLYCLONAL ANTIBODY

RESTRICTION MAP OF THE 19 kDa PROTEIN
AND CONSTRUCTION OF THE EXPRESSION VECTOR

SOLID BOX : HISTIDINE TAG REGION

SHADED BOX : SECRETION SIGNAL PEPTIDE REGION

OPEN : GENE CODING REGION

RESTRICTION MAP OF THE 35 kDa PROTEIN
AND CONSTRUCTION OF THE EXPRESSION VECTOR

SOLID BOX : HISTIDINE TAG REGION

SHADED BOX : SECRETION SIGNAL PEPTIDE REGION

OPEN : GENE CODING REGION

SEQUENCE LISTING

```
<160> NUMBER OF SEQ ID NOS: 40

<210> SEQ ID NO 1
<211> LENGTH: 866
<212> TYPE: DNA
<213> ORGANISM: Oplophorus gracilorostris
<220> FEATURE:
<221> NAME/KEY: CDS
<222> LOCATION: (46)..(633)
<223> OTHER INFORMATION:

<400> SEQUENCE: 1
tgtttgggtt ataggtggta tatcattaac tctacttgag agaag atg gcg tac tcc        57
                                                 Met Ala Tyr Ser
                                                 1 act ctg ttc ata att gca ttg acc gcc gtt gtc act caa gct tcc tca       105
Thr Leu Phe Ile Ile Ala Leu Thr Ala Val Val Thr Gln Ala Ser Ser
5                   10                  15                  20 act caa aaa tct aac cta act ttt acg ttg gca gat ttc gtt gga gac       153
Thr Gln Lys Ser Asn Leu Thr Phe Thr Leu Ala Asp Phe Val Gly Asp
                25                  30                  35 tgg caa cag aca gct gga tac aac caa gat caa gtg tta gaa caa gga       201
Trp Gln Gln Thr Ala Gly Tyr Asn Gln Asp Gln Val Leu Glu Gln Gly
            40                  45                  50 gga ttg tct agt ctg ttc caa gcc ctg gga gtg tca gtc acg ccc ata       249
Gly Leu Ser Ser Leu Phe Gln Ala Leu Gly Val Ser Val Thr Pro Ile
        55                  60                  65 cag aaa gtt gta ctg tct ggg gag aat ggg tta aaa gct gat att cat       297
Gln Lys Val Val Leu Ser Gly Glu Asn Gly Leu Lys Ala Asp Ile His
```

```
                70                  75                  80
gtc ata ata cct tac gag gga ctc agt ggt ttt caa atg ggt cta att        345
Val Ile Ile Pro Tyr Glu Gly Leu Ser Gly Phe Gln Met Gly Leu Ile
 85                  90                  95                 100 gaa atg atc ttc aaa gtt gtt tac ccc gtg gat gat cat cat ttc aag        393
Glu Met Ile Phe Lys Val Val Tyr Pro Val Asp Asp His His Phe Lys
                    105                 110                 115 att att ctc cat tat ggt aca ctc gtt att gac ggt gta aca ccc aac        441
Ile Ile Leu His Tyr Gly Thr Leu Val Ile Asp Gly Val Thr Pro Asn
                    120                 125                 130 atg att gac tac ttt gga aga cct tac cct gga att gct gta ttt gac        489
Met Ile Asp Tyr Phe Gly Arg Pro Tyr Pro Gly Ile Ala Val Phe Asp
            135                 140                 145 ggc aag cag atc aca gtt act gga act ctg tgg aac ggc aac aag atc        537
Gly Lys Gln Ile Thr Val Thr Gly Thr Leu Trp Asn Gly Asn Lys Ile
150                 155                 160 tat gat gag agg cta atc aac cct gat ggt tca ctc ctc ttc aga gtt        585
Tyr Asp Glu Arg Leu Ile Asn Pro Asp Gly Ser Leu Leu Phe Arg Val
165                 170                 175                 180 act atc aat gga gtc acg gga tgg agg ctt tgc gag aac att ctt gcc        633
Thr Ile Asn Gly Val Thr Gly Trp Arg Leu Cys Glu Asn Ile Leu Ala
                185                 190                 195 taaattacat ctcgagaatt gcttaaagcc tttttatgtc tataaattgg agtggaaaat      693
gtataataca tatgattttt aggacagtta ttttatttaa ttgctcactt aaatttaaat      753
ctgaagacca ctataactgt tcagaatgga actgtagtca aactgtatta aatgcattaa      813
agatcttatc atatgattta gaaaaaaaaa aaaaaaaaaa ataaaaaaaa aaa             866

<210> SEQ ID NO 2
<211> LENGTH: 196
<212> TYPE: PRT
<213> ORGANISM: Oplophorus gracilorostris

<400> SEQUENCE: 2

Met Ala Tyr Ser Thr Leu Phe Ile Ile Ala Leu Thr Ala Val Val Thr
 1               5                  10                  15

Gln Ala Ser Ser Thr Gln Lys Ser Asn Leu Thr Phe Thr Leu Ala Asp
                20                  25                  30

Phe Val Gly Asp Trp Gln Gln Thr Ala Gly Tyr Asn Gln Asp Gln Val
            35                  40                  45

Leu Glu Gln Gly Gly Leu Ser Ser Leu Phe Gln Ala Leu Gly Val Ser
 50                  55                  60

Val Thr Pro Ile Gln Lys Val Val Leu Ser Gly Glu Asn Gly Leu Lys
 65                  70                  75                  80

Ala Asp Ile His Val Ile Pro Tyr Glu Gly Leu Ser Gly Phe Gln
                85                  90                  95

Met Gly Leu Ile Glu Met Ile Phe Lys Val Val Tyr Pro Val Asp Asp
                100                 105                 110

His His Phe Lys Ile Ile Leu His Tyr Gly Thr Leu Val Ile Asp Gly
            115                 120                 125

Val Thr Pro Asn Met Ile Asp Tyr Phe Gly Arg Pro Tyr Pro Gly Ile
130                 135                 140

Ala Val Phe Asp Gly Lys Gln Ile Thr Val Thr Gly Thr Leu Trp Asn
145                 150                 155                 160

Gly Asn Lys Ile Tyr Asp Glu Arg Leu Ile Asn Pro Asp Gly Ser Leu
                165                 170                 175
```

```
Leu Phe Arg Val Thr Ile Asn Gly Val Thr Gly Trp Arg Leu Cys Glu
            180                 185                 190

Asn Ile Leu Ala
        195

<210> SEQ ID NO 3
<211> LENGTH: 1292
<212> TYPE: DNA
<213> ORGANISM: Oplophorus gracilorostris
<220> FEATURE:
<221> NAME/KEY: CDS
<222> LOCATION: (79)..(1155)
<223> OTHER INFORMATION:

<400> SEQUENCE: 3
tagcgtagct gcatcctggt gtcgtcgacc ctctccagca tcatcatctg tggaagttcg      60
aacatctcgc agagcaaa atg gct gtc aac ttc aag ttt agc ctc ctt acc      111
                    Met Ala Val Asn Phe Lys Phe Ser Leu Leu Thr
                      1               5                      10 ata acc att gtt gtt aat atc tta gtc tat tgc aat gca tca gca att      159
Ile Thr Ile Val Val Asn Ile Leu Val Tyr Cys Asn Ala Ser Ala Ile
            15                  20                  25 aaa ttc gat gtt gat ttg gag aag gtt ccc tct aat gct gtt gcc tgt      207
Lys Phe Asp Val Asp Leu Glu Lys Val Pro Ser Asn Ala Val Ala Cys
        30                  35                  40 cct gca gcc gaa gat att gcc cct tgc acc tgc aaa gtg ggt gaa ggc      255
Pro Ala Ala Glu Asp Ile Ala Pro Cys Thr Cys Lys Val Gly Glu Gly
    45                  50                  55 gac gtt atg gat atg gat tgc tcc aaa gta aca agt gac gct gaa ctt      303
Asp Val Met Asp Met Asp Cys Ser Lys Val Thr Ser Asp Ala Glu Leu
60                  65                  70                  75 gct tcc ata ttt agt aaa acg ttt ccc tct aac acc ttc cgt gaa tta      351
Ala Ser Ile Phe Ser Lys Thr Phe Pro Ser Asn Thr Phe Arg Glu Leu
                80                  85                  90 ttt att gaa ttc aat cgc gag att acg act ctg aca gct gat agt ttg      399
Phe Ile Glu Phe Asn Arg Glu Ile Thr Thr Leu Thr Ala Asp Ser Leu
            95                 100                 105 gga gca gca aca ttt aca aaa atc gct att act agt tgt act caa ttg      447
Gly Ala Ala Thr Phe Thr Lys Ile Ala Ile Thr Ser Cys Thr Gln Leu
        110                 115                 120 aag acc ata gaa gaa aat gct ttt atg gcc agt gct gcc aca ctc gag      495
Lys Thr Ile Glu Glu Asn Ala Phe Met Ala Ser Ala Ala Thr Leu Glu
    125                 130                 135 aaa ctc gtg ctc tta aaa aat gat ctt tcc tct ttt cct ttt gaa gaa      543
Lys Leu Val Leu Leu Lys Asn Asp Leu Ser Ser Phe Pro Phe Glu Glu
140                 145                 150                 155 atg tca caa tac aca aaa tta aat tgg ctt gaa tta tcc gta aat agc      591
Met Ser Gln Tyr Thr Lys Leu Asn Trp Leu Glu Leu Ser Val Asn Ser
                160                 165                 170 att aca gga tgg cca gct ctc tca tcg gat aca cta gct aac ctt att      639
Ile Thr Gly Trp Pro Ala Leu Ser Ser Asp Thr Leu Ala Asn Leu Ile
            175                 180                 185 ttg ttc cgt aat cct att ggt aat att cca gtt gat gcc ttc cag act      687
Leu Phe Arg Asn Pro Ile Gly Asn Ile Pro Val Asp Ala Phe Gln Thr
        190                 195                 200 ctt cct aat atc gaa caa ttc aac tgc ttc gat tgt agc atc acc gaa      735
Leu Pro Asn Ile Glu Gln Phe Asn Cys Phe Asp Cys Ser Ile Thr Glu
    205                 210                 215 gtg gaa gca ggt act ttt act aga tca cca aaa ctc caa aag ctt gtg      783
Val Glu Ala Gly Thr Phe Thr Arg Ser Pro Lys Leu Gln Lys Leu Val
220                 225                 230                 235
```

```
tta ggt tat aac ggt ctg act agc ctt ccc gta ggc gcc atc aaa ctc         831
Leu Gly Tyr Asn Gly Leu Thr Ser Leu Pro Val Gly Ala Ile Lys Leu
            240                 245                 250 cat gga cat ggc cca acc act tcc aac ttg ggt atc acc aat aat cag         879
His Gly His Gly Pro Thr Thr Ser Asn Leu Gly Ile Thr Asn Asn Gln
            255                 260                 265 atc atc agt ttc ccc gag ggt gct gtt gaa ggc atc caa ggc atc ctt         927
Ile Ile Ser Phe Pro Glu Gly Ala Val Glu Gly Ile Gln Gly Ile Leu
            270                 275                 280 gga att gac ttt aat cgt gta aca tct cta agt gag gaa gtg tgg cga         975
Gly Ile Asp Phe Asn Arg Val Thr Ser Leu Ser Glu Glu Val Trp Arg
    285                 290                 295 cca att tta gaa aat ctt ttc caa ttc agc ttg ctt aac aac cca cta        1023
Pro Ile Leu Glu Asn Leu Phe Gln Phe Ser Leu Leu Asn Asn Pro Leu
300                 305                 310                 315 gca tgt gta tgt gac gta atg tgg ctt att gat agc cca gaa ttg ctg        1071
Ala Cys Val Cys Asp Val Met Trp Leu Ile Asp Ser Pro Glu Leu Leu
            320                 325                 330 gca aaa att aaa ggc aat ccc cga tgt gcc ggt gga aaa aga ctc aag        1119
Ala Lys Ile Lys Gly Asn Pro Arg Cys Ala Gly Gly Lys Arg Leu Lys
            335                 340                 345 aat ttg gat cca gct gtt ttc cat gca atg tgc caa taagaagaag            1165
Asn Leu Asp Pro Ala Val Phe His Ala Met Cys Gln
            350                 355 aagaagaatt gagtcctcct gtatctactt ctgaagaaga agaagaagaa gaatcattaa     1225
aataacaact aatattttt aaatataaat cacaatgtat ttatacagtg tagtggcaaa      1285
tacagta                                                               1292
```

<210> SEQ ID NO 4
<211> LENGTH: 359
<212> TYPE: PRT
<213> ORGANISM: Oplophorus gracilorostris

<400> SEQUENCE: 4

```
Met Ala Val Asn Phe Lys Phe Ser Leu Leu Thr Ile Thr Ile Val Val
1               5                   10                  15

Asn Ile Leu Val Tyr Cys Asn Ala Ser Ala Ile Lys Phe Asp Val Asp
            20                  25                  30

Leu Glu Lys Val Pro Ser Asn Ala Val Ala Cys Pro Ala Ala Glu Asp
        35                  40                  45

Ile Ala Pro Cys Thr Cys Lys Val Gly Glu Gly Asp Val Met Asp Met
    50                  55                  60

Asp Cys Ser Lys Val Thr Ser Asp Ala Glu Leu Ala Ser Ile Phe Ser
65                  70                  75                  80

Lys Thr Phe Pro Ser Asn Thr Phe Arg Glu Leu Phe Ile Glu Phe Asn
                85                  90                  95

Arg Glu Ile Thr Thr Leu Thr Ala Asp Ser Leu Gly Ala Ala Thr Phe
            100                 105                 110

Thr Lys Ile Ala Ile Thr Ser Cys Thr Gln Leu Lys Thr Ile Glu Glu
        115                 120                 125

Asn Ala Phe Met Ala Ser Ala Thr Leu Glu Lys Leu Val Leu Leu
    130                 135                 140

Lys Asn Asp Leu Ser Ser Phe Pro Phe Glu Glu Met Ser Gln Tyr Thr
145                 150                 155                 160

Lys Leu Asn Trp Leu Glu Leu Ser Val Asn Ser Ile Thr Gly Trp Pro
                165                 170                 175
```

```
Ala Leu Ser Ser Asp Thr Leu Ala Asn Leu Ile Leu Phe Arg Asn Pro
            180                 185                 190

Ile Gly Asn Ile Pro Val Asp Ala Phe Gln Thr Leu Pro Asn Ile Glu
        195                 200                 205

Gln Phe Asn Cys Phe Asp Cys Ser Ile Thr Glu Val Glu Ala Gly Thr
        210                 215                 220

Phe Thr Arg Ser Pro Lys Leu Gln Lys Leu Val Leu Gly Tyr Asn Gly
225                 230                 235                 240

Leu Thr Ser Leu Pro Val Gly Ala Ile Lys Leu His Gly His Gly Pro
            245                 250                 255

Thr Thr Ser Asn Leu Gly Ile Thr Asn Asn Gln Ile Ile Ser Phe Pro
            260                 265                 270

Glu Gly Ala Val Glu Gly Ile Gln Gly Ile Leu Gly Ile Asp Phe Asn
        275                 280                 285

Arg Val Thr Ser Leu Ser Glu Val Trp Arg Pro Ile Leu Glu Asn
        290                 295                 300

Leu Phe Gln Phe Ser Leu Leu Asn Asn Pro Leu Ala Cys Val Cys Asp
305                 310                 315                 320

Val Met Trp Leu Ile Asp Ser Pro Glu Leu Leu Ala Lys Ile Lys Gly
                325                 330                 335

Asn Pro Arg Cys Ala Gly Gly Lys Arg Leu Lys Asn Leu Asp Pro Ala
            340                 345                 350

Val Phe His Ala Met Cys Gln
            355

<210> SEQ ID NO 5
<211> LENGTH: 28
<212> TYPE: PRT
<213> ORGANISM: Oplophorus gracilorostris

<400> SEQUENCE: 5

Phe Thr Leu Ala Asp Phe Val Gly Asp Trp Gln Gln Thr Ala Gly Tyr
1               5                   10                  15

Asn Gln Asp Gln Val Leu Glu Gln Gly Gly Leu Ser
            20                  25

<210> SEQ ID NO 6
<211> LENGTH: 29
<212> TYPE: PRT
<213> ORGANISM: Oplophorus gracilorostris
<220> FEATURE:
<221> NAME/KEY: MISC_FEATURE
<222> LOCATION: (4)..(4)
<223> OTHER INFORMATION: Xaa = any amino acid
<220> FEATURE:
<221> NAME/KEY: MISC_FEATURE
<222> LOCATION: (13)..(13)
<223> OTHER INFORMATION: Xaa = any amino acid
<220> FEATURE:
<221> NAME/KEY: MISC_FEATURE
<222> LOCATION: (15)..(15)
<223> OTHER INFORMATION: Xaa = any amino acid
<220> FEATURE:
<221> NAME/KEY: MISC_FEATURE
<222> LOCATION: (27)..(27)
<223> OTHER INFORMATION: Xaa = any amino acid

<400> SEQUENCE: 6

Ala Val Ala Xaa Pro Ala Ala Glu Asp Ile Ala Pro Xaa Thr Xaa Lys
1               5                   10                  15

Val Gly Glu Gly Asp Val Met Asp Met Asp Xaa Ser Lys
```

<210> SEQ ID NO 7
<211> LENGTH: 16
<212> TYPE: PRT
<213> ORGANISM: Oplophorus gracilorostris

<400> SEQUENCE: 7

Val Thr Ser Asp Ala Glu Leu Ala Ser Ile Phe Ser Lys Thr Phe Pro
1               5                   10                  15

<210> SEQ ID NO 8
<211> LENGTH: 16
<212> TYPE: PRT
<213> ORGANISM: Oplophorus gracilorostris

<400> SEQUENCE: 8

Asn Asp Leu Ser Ser Phe Pro Phe Glu Glu Met Ser Gln Tyr Thr Lys
1               5                   10                  15

<210> SEQ ID NO 9
<211> LENGTH: 16
<212> TYPE: PRT
<213> ORGANISM: Oplophorus gracilorostris

<400> SEQUENCE: 9

Leu Val Leu Gly Tyr Asn Gly Leu Thr Ser Leu Pro Val Gly Ala Ile
1               5                   10                  15

<210> SEQ ID NO 10
<211> LENGTH: 12
<212> TYPE: PRT
<213> ORGANISM: Oplophorus gracilorostris
<220> FEATURE:
<221> NAME/KEY: MISC_FEATURE
<222> LOCATION: (11)..(11)
<223> OTHER INFORMATION: Xaa = any amino acid

<400> SEQUENCE: 10

Asn Leu Asp Pro Ala Val Phe His Ala Met Xaa Gln
1               5                   10

<210> SEQ ID NO 11
<211> LENGTH: 7
<212> TYPE: PRT
<213> ORGANISM: Oplophorus gracilorostris

<400> SEQUENCE: 11

Ala Gly Tyr Asn Gln Asp Gln
1               5

<210> SEQ ID NO 12
<211> LENGTH: 7
<212> TYPE: PRT
<213> ORGANISM: Oplophorus gracilorostris

<400> SEQUENCE: 12

Gly Asp Val Met Asp Met Asp
1               5

<210> SEQ ID NO 13
<211> LENGTH: 20
<212> TYPE: DNA
<213> ORGANISM: Artificial Sequence
<220> FEATURE:
<223> OTHER INFORMATION: Synthetic DNA

```
<220> FEATURE:
<221> NAME/KEY: misc_feature
<222> LOCATION: (3)..(3)
<223> OTHER INFORMATION: n = a, c, g, or t
<220> FEATURE:
<221> NAME/KEY: misc_feature
<222> LOCATION: (6)..(6)
<223> OTHER INFORMATION: n = a, c, g, or t

<400> SEQUENCE: 13
gcnggntaya aycargayca                                             20

<210> SEQ ID NO 14
<211> LENGTH: 20
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (3)..(3)
<223> OTHER INFORMATION: n = a, c, g, or t
<220> FEATURE:
<221> NAME/KEY: misc_feature
<222> LOCATION: (9)..(9)
<223> OTHER INFORMATION: n = a, c, g, or t

<400> SEQUENCE: 14
gtngtygtna tggayatgtc                                             20

<210> SEQ ID NO 15
<211> LENGTH: 33
<212> TYPE: DNA
<213> ORGANISM: Artificial Sequence
<220> FEATURE:
<223> OTHER INFORMATION: Synthetic DNA

<400> SEQUENCE: 15
ccggctagct ttacgttggc agatttcgtt gga                              33

<210> SEQ ID NO 16
<211> LENGTH: 20
<212> TYPE: DNA
<213> ORGANISM: Artificial Sequence
<220> FEATURE:
<223> OTHER INFORMATION: Synthetic DNA

<400> SEQUENCE: 16
taatacgact cactataggg                                             20

<210> SEQ ID NO 17
<211> LENGTH: 30
<212> TYPE: DNA
<213> ORGANISM: Artificial Sequence
<220> FEATURE:
<223> OTHER INFORMATION: Synthetic DNA

<400> SEQUENCE: 17
ccgtctagag ctgttgcctg tcctgcagcc                                  30

<210> SEQ ID NO 18
<211> LENGTH: 30
<212> TYPE: DNA
<213> ORGANISM: Artificial Sequence
<220> FEATURE:
<223> OTHER INFORMATION: Synthetic DNA

<400> SEQUENCE: 18
```
gccgtcgact tattggcaca ttgcatggaa                                    30

<210> SEQ ID NO 19
<211> LENGTH: 37
<212> TYPE: DNA
<213> ORGANISM: Artificial Sequence
<220> FEATURE:
<223> OTHER INFORMATION: Synthetic DNA

<400> SEQUENCE: 19
ccggctagcc accatggcgt actccactct gttcata                            37

<210> SEQ ID NO 20
<211> LENGTH: 40
<212> TYPE: DNA
<213> ORGANISM: Artificial Sequence
<220> FEATURE:
<223> OTHER INFORMATION: Synthetic DNA

<400> SEQUENCE: 20
ccggctagcc accatgttta cgttggcaga tttcgttgga                         40

<210> SEQ ID NO 21
<211> LENGTH: 38
<212> TYPE: DNA
<213> ORGANISM: Artificial Sequence
<220> FEATURE:
<223> OTHER INFORMATION: Synthetic DNA

<400> SEQUENCE: 21
ccgctctaga attaggcaag aatgttctcg caaagcct                           38

<210> SEQ ID NO 22
<211> LENGTH: 34
<212> TYPE: DNA
<213> ORGANISM: Artificial Sequence
<220> FEATURE:
<223> OTHER INFORMATION: Synthetic DNA

<400> SEQUENCE: 22
ccggctagcc accatggctg tcaacttcaa gttt                               34

<210> SEQ ID NO 23
<211> LENGTH: 37
<212> TYPE: DNA
<213> ORGANISM: Artificial Sequence
<220> FEATURE:
<223> OTHER INFORMATION: Synthetic DNA

<400> SEQUENCE: 23
ccggctagcc accatggctg ttgcctgtcc tgcagcc                            37

<210> SEQ ID NO 24
<211> LENGTH: 32
<212> TYPE: DNA
<213> ORGANISM: Artificial Sequence
<220> FEATURE:
<223> OTHER INFORMATION: Synthetic DNA

<400> SEQUENCE: 24
ccgctctaga attattggca cattgcatgg aa                                 32

<210> SEQ ID NO 25
<211> LENGTH: 23
<212> TYPE: PRT
<213> ORGANISM: Oplophorus gracilorostris

```
<400> SEQUENCE: 25

Ala Val Ala Cys Pro Ala Ala Glu Asp Ile Ala Pro Cys Thr Cys Lys
1               5                   10                  15

Val Gly Glu Gly Asp Val Met
            20

<210> SEQ ID NO 26
<211> LENGTH: 24
<212> TYPE: PRT
<213> ORGANISM: Oplophorus gracilorostris

<400> SEQUENCE: 26

Asp Met Asp Cys Ser Lys Val Thr Ser Asp Ala Glu Leu Ala Ser Ile
1               5                   10                  15

Phe Ser Lys Thr Phe Pro Ser Asn
            20

<210> SEQ ID NO 27
<211> LENGTH: 24
<212> TYPE: PRT
<213> ORGANISM: Oplophorus gracilorostris

<400> SEQUENCE: 27

Thr Phe Arg Glu Leu Phe Ile Glu Phe Asn Arg Glu Ile Thr Thr Leu
1               5                   10                  15

Thr Ala Asp Ser Leu Gly Ala Ala
            20

<210> SEQ ID NO 28
<211> LENGTH: 26
<212> TYPE: PRT
<213> ORGANISM: Oplophorus gracilorostris

<400> SEQUENCE: 28

Thr Phe Thr Lys Ile Ala Ile Thr Ser Cys Thr Gln Leu Lys Thr Ile
1               5                   10                  15
Glu Glu Asn Ala Phe Met Ala Ser Ala Ala
            20                  25

<210> SEQ ID NO 29
<211> LENGTH: 24
<212> TYPE: PRT
<213> ORGANISM: Oplophorus gracilorostris

<400> SEQUENCE: 29

Thr Leu Glu Lys Leu Val Leu Leu Lys Asn Asp Leu Ser Ser Phe Pro
1               5                   10                  15

Phe Glu Glu Met Ser Gln Tyr Thr
            20

<210> SEQ ID NO 30
<211> LENGTH: 21
<212> TYPE: PRT
<213> ORGANISM: Oplophorus gracilorostris

<400> SEQUENCE: 30

Lys Leu Asn Trp Leu Glu Leu Ser Val Asn Ser Ile Thr Gly Trp Pro
1               5                   10                  15

Ala Leu Ser Ser Asp
            20
```

```
<210> SEQ ID NO 31
<211> LENGTH: 24
<212> TYPE: PRT
<213> ORGANISM: Oplophorus gracilorostris

<400> SEQUENCE: 31

Thr Leu Ala Asn Leu Ile Leu Phe Arg Asn Pro Ile Gly Asn Ile Pro
1               5                   10                  15

Val Asp Ala Phe Gln Thr Leu Pro
            20

<210> SEQ ID NO 32
<211> LENGTH: 24
<212> TYPE: PRT
<213> ORGANISM: Oplophorus gracilorostris

<400> SEQUENCE: 32

Asn Ile Glu Gln Phe Asn Cys Phe Asp Cys Ser Ile Thr Glu Val Glu
1               5                   10                  15

Ala Gly Thr Phe Thr Arg Ser Pro
            20

<210> SEQ ID NO 33
<211> LENGTH: 27
<212> TYPE: PRT
<213> ORGANISM: Oplophorus gracilorostris

<400> SEQUENCE: 33

Lys Leu Gln Lys Leu Val Leu Gly Tyr Asn Gly Leu Thr Ser Leu Pro
1               5                   10                  15

Val Gly Ala Ile Lys Leu His Gly His Gly Pro
            20                  25

<210> SEQ ID NO 34
<211> LENGTH: 24
<212> TYPE: PRT
<213> ORGANISM: Oplophorus gracilorostris

<400> SEQUENCE: 34

Thr Thr Ser Asn Leu Gly Ile Thr Asn Asn Gln Ile Ile Ser Phe Pro
1               5                   10                  15

Glu Gly Ala Val Glu Gly Ile Gln
            20

<210> SEQ ID NO 35
<211> LENGTH: 23
<212> TYPE: PRT
<213> ORGANISM: Oplophorus gracilorostris

<400> SEQUENCE: 35

Gly Ile Leu Gly Ile Asp Phe Asn Arg Val Thr Ser Leu Ser Glu Glu
1               5                   10                  15

Val Trp Arg Pro Ile Leu Glu
            20

<210> SEQ ID NO 36
<211> LENGTH: 25
<212> TYPE: PRT
<213> ORGANISM: Oplophorus gracilorostris

<400> SEQUENCE: 36

Asn Leu Phe Gln Phe Ser Leu Leu Asn Asn Pro Leu Ala Cys Val Cys
1               5                   10                  15
```

Asp Val Met Trp Leu Ile Asp Ser Pro
            20                  25

<210> SEQ ID NO 37
<211> LENGTH: 23
<212> TYPE: PRT
<213> ORGANISM: Oplophorus gracilorostris

<400> SEQUENCE: 37

Glu Leu Leu Ala Lys Ile Lys Gly Asn Pro Arg Cys Ala Gly Gly Lys
1               5                   10                  15

Arg Leu Lys Asn Leu Asp Pro
            20

<210> SEQ ID NO 38
<211> LENGTH: 8
<212> TYPE: PRT
<213> ORGANISM: Oplophorus gracilorostris

<400> SEQUENCE: 38

Ala Val Phe His Ala Met Cys Gln
1               5

<210> SEQ ID NO 39
<211> LENGTH: 15
<212> TYPE: PRT
<213> ORGANISM: Oplophorus gracilorostris
<220> FEATURE:
<221> NAME/KEY: MISC_FEATURE
<222> LOCATION: (1)..(1)
<223> OTHER INFORMATION: Xaa = Leu or Ile
<220> FEATURE:
<221> NAME/KEY: MISC_FEATURE
<222> LOCATION: (2)..(3)
<223> OTHER INFORMATION: Xaa = any amino acid
<220> FEATURE:
<221> NAME/KEY: MISC_FEATURE
<222> LOCATION: (5)..(5)
<223> OTHER INFORMATION: Xaa = any amino acid
<220> FEATURE:
<221> NAME/KEY: MISC_FEATURE
<222> LOCATION: (6)..(6)
<223> OTHER INFORMATION: Xaa = Leu or Ile
<220> FEATURE:
<221> NAME/KEY: MISC_FEATURE
<222> LOCATION: (7)..(8)
<223> OTHER INFORMATION: Xaa = any amino acid
<220> FEATURE:
<221> NAME/KEY: MISC_FEATURE
<222> LOCATION: (10)..(10)
<223> OTHER INFORMATION: Xaa = any amino acid
<220> FEATURE:
<221> NAME/KEY: MISC_FEATURE
<222> LOCATION: (11)..(11)
<223> OTHER INFORMATION: Xaa = Leu or Ile
<220> FEATURE:
<221> NAME/KEY: MISC_FEATURE
<222> LOCATION: (12)..(14)
<223> OTHER INFORMATION: Xaa = any amino acid

<400> SEQUENCE: 39

Xaa Xaa Xaa Leu Xaa Xaa Xaa Xaa Asn Xaa Xaa Xaa Xaa Xaa Pro
1               5                   10                  15

<210> SEQ ID NO 40
<211> LENGTH: 24
<212> TYPE: PRT
<213> ORGANISM: Oplophorus gracilorostris
<220> FEATURE:
<221> NAME/KEY: MISC_FEATURE

```
-continued

<222> LOCATION: (1)..(1)
<223> OTHER INFORMATION: Xaa = any amino acid
<220> FEATURE:
<221> NAME/KEY: MISC_FEATURE
<222> LOCATION: (2)..(2)
<223> OTHER INFORMATION: Xaa = Leu or Ile
<220> FEATURE:
<221> NAME/KEY: MISC_FEATURE
<222> LOCATION: (3)..(4)
<223> OTHER INFORMATION: Xaa = any amino acid
<220> FEATURE:
<221> NAME/KEY: MISC_FEATURE
<222> LOCATION: (6)..(6)
<223> OTHER INFORMATION: Xaa = any amino acid
<220> FEATURE:
<221> NAME/KEY: MISC_FEATURE
<222> LOCATION: (7)..(7)
<223> OTHER INFORMATION: Xaa = Leu or Ile
<220> FEATURE:
<221> NAME/KEY: MISC_FEATURE
<222> LOCATION: (8)..(9)
<223> OTHER INFORMATION: Xaa = any amino acid
<220> FEATURE:
<221> NAME/KEY: MISC_FEATURE
<222> LOCATION: (11)..(11)
<223> OTHER INFORMATION: Xaa = any amino acid
<220> FEATURE:
<221> NAME/KEY: MISC_FEATURE
<222> LOCATION: (12)..(12)
<223> OTHER INFORMATION: Xaa = Leu or Ile
<220> FEATURE:
<221> NAME/KEY: MISC_FEATURE
<222> LOCATION: (13)..(15)
<223> OTHER INFORMATION: Xaa = any amino acid
<220> FEATURE:
<221> NAME/KEY: MISC_FEATURE
<222> LOCATION: (17)..(24)
<223> OTHER INFORMATION: Xaa = any amino acid

<400> SEQUENCE: 40

Xaa Xaa Xaa Xaa Leu Xaa Xaa Xaa Xaa Asn Xaa Xaa Xaa Xaa Xaa Pro
1               5                   10                  15

Xaa Xaa Xaa Xaa Xaa Xaa Xaa Xaa
            20
```

OPLOPHORUS LUCIFERASE SUBUNITS

FIELD OF THE INVENTION

The present invention relates to a novel luciferase derived from Decapoda. More specifically, the invention relates to a secretional luciferase from *Oplophorus gracilirostris*, which is composed of 19 kDa and 35 kDa proteins. The invention also relates to polynucleotides encoding at least one of these proteins, a recombinant expression vector comprising at least one of these polynucleotides, a host cell transformed with said vector, and process for producing said photoprotein.

BACKGROUND OF THE INVENTION

The genes encoding luciferases or photoproteins which have been reported are listed in Table 1.

TABLE 1

Reported genes of photoproteins and luciferases

| Protein | Origin | Discoverer (publication year) | Gene Accession No. |
|---|---|---|---|
| 1. Photoprotein | | | |
| Aequorin | *Aequorea victoria* | Inouye et al. (1985) | AEVAQ440X: L29571 |
| | *Aequorea victoria* | Prasher et al. (1987) | AEVAEQA: M16103 |
| Clytin | *Clytia gregarium* | Inouye & Tsuji (1993) | CY1APOCLYT: L13247 |
| Mitrocomin | *Mitrocoma cellularia* | Fagan et al. (1993) | MITMI17: L31623 |
| Obelin | *Obelia longissima* | Illarionov et al. (1995) | OLU07128: U07128 |
| 2. Luciferase | | | |
| Firefly | *Photinus pyralis* | de Wet et al. (1987) | PPYLUC: M15077 |
| | *Luciola cruciata* | Matuda et al. (1989) | FFLLUC: M26194 |
| | *Luciola lateralis* | Tatsumi et al. (1992) | LLUCI: X66919 |
| | *Luciola lateralis* | Cho et al. (1995) | LLLUCIFMJ: Z49891 |
| | *Luciola mingrelica* | Devine et al. (1993) | |
| | *Photuris pennsylvanica* | Zenno et al. (1993) | D25415: D25415 |
| | *Photuris pennsylvanica* | Ye et al. (1997) | PPU31240: U31240 |
| | *Pyrocoelia miyako* | Ohmiya et al. (1995) | PIBLUCA: L39928 |
| | *Hotaria parvula* | Ohmiya et al. (1995) | HOTLUCI: L39929 |
| Glow worm | *Lampyris noctiluca* | Sala-Newby et al. (1996) | LNLUCPROT: X89479 |
| Click beetle | *Pyrophorus plagiophthalamus* | Wood et al. (1989) | |
| Railroad-worm | *Phrixothrix vivianii* | Viviani et al. (1999) | AF139644: AF139644 |
| | *Phrixothrix hirtus* | Viviani et al. (1999) | AF139645: AF139645 |
| Vargula | *Vargula hilgendorfii* | Kazami et al. (1988) | Pat. Appln. No. JP63-199295 |
| | | Thompson et al. (1989) | VAHLUC: M25666 |
| Renilla | *Renilla reniformis* | Lorenz et al. (1991) | RELLUC: M63501 |
| Gonyaulax | *Gonyaulax polyedra* | Bae & Hastings (1994) | GONLUCA: L04648 |
| Bacteria | *Vibrio fischeri* | Foran & Brown (1988) | VFLUXAB: X06758 |

TABLE 1-continued

Reported genes of photoproteins and luciferases

| Protein | Origin | Discoverer (publication year) | Gene Accession No. |
|---|---|---|---|
| | *Vibrio harveyi* | Cohn et al. (1985) | VIBHALUXA: M10961 |
| | | Johnston et al. (1986) | VIBHALUXA: M10961 |
| | *Photobacterium leiogathis* | Illarionov et al. (1988) | PLLUXABG: X08036 |
| | | Lee et al. (1991) | PHRLUX: M63594 |
| | *Photobacterium phosphoreum* | Ferri et al. (1991) | PHRLUXABDF: M65067 |
| | *Xenorhabdus luminescence* | Johnston et al. (1990) | XENLUXABB: M55977 |
| | | Szittner & Meighen (1990) | XENLUXAB: M57416 |
| | *Kryptophanaron alfredi* | Haygood (1986, 1990) | KRYLUC: M36597 |
| | *Alteromonas hanedai* | Zenno et al. (1994) | Pat. Appln. No. JP06-035450 |

These photoproteins and luciferases are an industrially important protein and have been utilized, for example, as a reporter enzyme. Various methods for detecting an analyte using luminescent reactions of these enzymes have been developed, and also some apparatuses to be used in these methods have been improved and widespread. Among these known photoproteins and luciferases, however, there is no enzyme applicable to extensive purposes. Consequently, one has to choose a proper enzyme for individual purpose.

Among the prior art luminescent substrates (often referred to as luciferin), those having the determined structures are only the substrates represented by formulas (1)–(8):

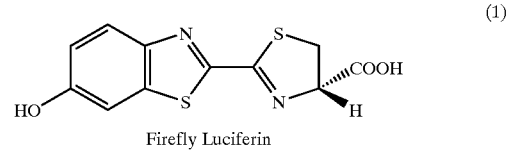

(1)

Firefly Luciferin

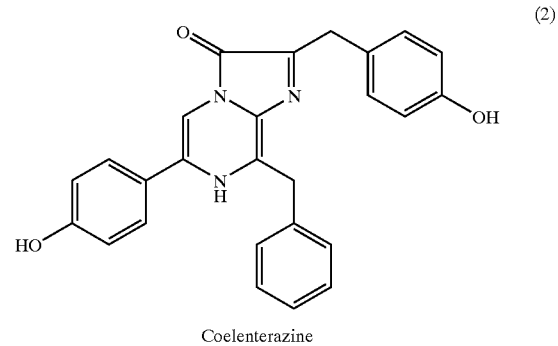

(2)

Coelenterazine

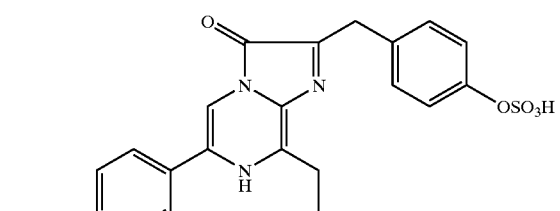

Watasenia Luciferin (3)

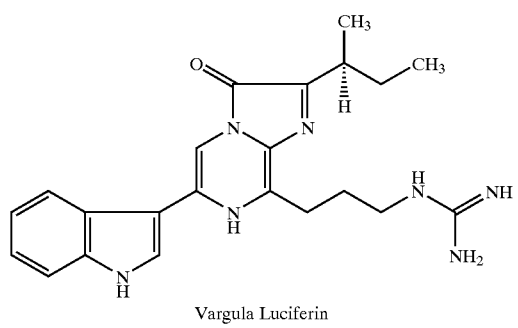

Vargula Luciferin (4)

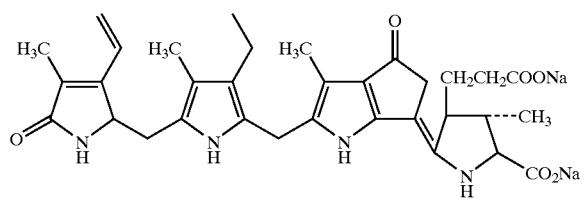

Flagellata Luciferin (5)

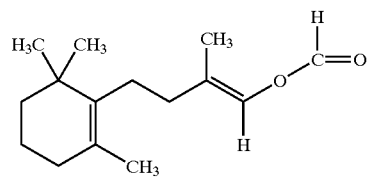

Latia Luciferin (6)

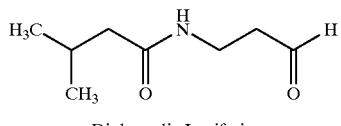

Diplocardia Luciferin (7)

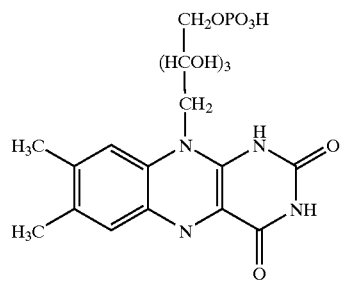

Reduced form Flavin mononucleotide (8)

The luminescent substrates include species specific and species non-specific substrates. The minimum unit in the enzymatic bioluminescent reaction consists of a luminescent enzyme (luciferase), a luminescent substrate (luciferin) and molecular oxygen. A luminescent reaction which requires other components such as a co-enzyme or a supplemental molecule is also reported.

Examples of the luciferase with luminescence in minimum unit include those derived from Renilla, Cypridina and Gonyaulax. The luciferins corresponding to these luciferases have very complicated structures as shown in the above formulas (4) and (5). The methods for synthesizing Cypridina and Gonyaulax luciferins are already known, but yield is remarkably low due to their complicated synthesizing process. Though the luciferins extracted from natural products are,also used, they are very expensive with little industrial utility.

On the contrary, Renilla luciferin known as coelenterazine and derivatives thereof are commercially available and inexpensive, because various methods for the production thereof have been established.

Among the photoproteins in Table 1, a secretional luciferase is only Cypridina luciferase. The structure of the gene is reported in Thompson, E. M., et al., Proc. Natl. Acad. Sci. USA, 86, 6567–6571 (1989) and the application of the gene is reported in Inouye, S., et al., Proc. Natl. Acad. Sci. USA, 89, 9584–9587 (1992).

In the construction of a bioassay system such as a drug screening system, the secretional luciferase has an industrial advantage in that the luminescence activity can be detected in living cells without cell disruption using the luciferase extracellularly secreted as a reporter. Generally, a secretional protein is not particularly difficult to produce if a suitable host-vector system is selected. Further, the purification of a recombinant protein from cultured media is easier in comparison with the purification from a cell extract. Thus, mass production of the secretional luciferase may advantageously hold down purification costs involved.

A particularly useful luciferase involves a luminescent system wherein the luminescent reaction occurs only among the minimal unit, i.e. a luciferase, a luciferin and molecular oxygen, the luciferin being coelenterazine or a derivative thereof which is readily available, and the luciferase itself being a secretional protein. A protein and a gene of such luciferase are advantageous not only scientifically but also industrially. However, isolation of gene encoding such luciferase and expression thereof in a living cell has not been reported yet.

A luciferase derived from a luminous shrimp belonging to Decapoda has been reported as a secretional luciferase, the luminescent substrate of which is coelenterazine. It is known that a luminous shrimp involves a secretional luciferase (enzyme) and that a blue luminescence is emitted by the reaction of the luciferase, a luminescent substrate luciferin and molecular oxygen.

The detailed classification of globally living luminous shrimps is disclosed in Herring, P. J., J. Mar. Biol. Ass. U.K., 56, 1029–1047 (1976). The only biochemical study of luciferase of luminous shrimp is reported by Shimomura et al., on a luciferase of the luminous shrimp *Oplophorus gracilirostris* living in the Suruga Bay, Sizuoka, Japan (Biochemistry, 17, 994–998 (1978)). This study report discloses a luciferase having a molecular weight of 130,000 which is composed of the tetramer of a polypeptide having a molecular weight of 31,000. The literature also reports that the luciferase has a quantum yield of 0.32 at 22° C., a high specific activity of $1.75 \times 10^{15}$ Photons/s. mg, an optimum light emission at 40° C. and an excellent heat stability. It also describes that the luminescent reaction proceeds in a wide range of pH.

The luciferin in the luminescent reaction of Oplophorus luciferase is coelenterazine represented by the above formula (2), which is also a luminescent substrate in the luminescent reactions of Renilla luciferase and a photoprotein, aequorin. The most important difference between these luminescent enzymes and Oplophorus luciferase is that Oplophorus luciferase has very broad substrate specificity in comparison with those of Renilla luciferase and aequorin. Oplophorus luciferase is more preferable than other luciferases, because it can utilize as a substrate bisdeoxycoelenterazine which is an analogue of coelenterazine and is available at a low cost.

However, either the protein structure or the gene structure of Oplophorus luciferase of a secretional type has not been elucidated. This is because living luminous shrimp, which are mostly living in the deep-sea, are very difficult to obtain in a large amount. Furthermore, population of the shrimp is decreasing due to the environmental changes. Therefore, construction of gene library from *Oplophorus gracilirostris* as well as early isolation of a gene encoding Oplophorus luciferase are desired.

SUMMARY OF THE INVENTION

An object of the present invention is to provide polynucleotides encoding Oplophorus luciferase and a luminescent subunit thereof.

Another object of the invention is to provide the recombinant secretional Oplophorus luciferase and the subunit encoded by the polynucleotides.

Another object of the invention is to provide an expression vector containing the polynucleotide(s) and a host transformed with the vector.

Further object of the invention is to provide a method for producing the recombinant Oplophorus luciferase or the recombinant photoprotein.

As a result of the isolation and purification of a secretional luciferase from *Oplophorus gracilirostris*, the present inventor found that Oplophorus luciferase is composed of 19 kDa and 35 kDa proteins. Then, the partial amino acid sequence of each protein was determined and the cloning of the proteins was carried out based on the information of their partial amino acid sequences. The genes coding for the two proteins was successfully cloned and the nucleotide sequences of the genes and the amino acid sequence of these proteins encoded by the gene could also be determined. Further, the present inventor has succeeded in preparing the expression vector containing the polynucleotide coding for each gene and a host such as a microorganism or a cultured animal cell which had been transformed with the vector. These proteins could be recombinantly produced by culturing the host cell or by in vitro translation system using the recombinant expression vector.

BRIEF DESCRIPTION OF THE DRAWINGS

FIG. 2 shows the alignment of the leucine-rich repeats structure of the 35 kDa Protein.

DETAILED DESCRIPTION OF THE INVENTION

Figure 1:
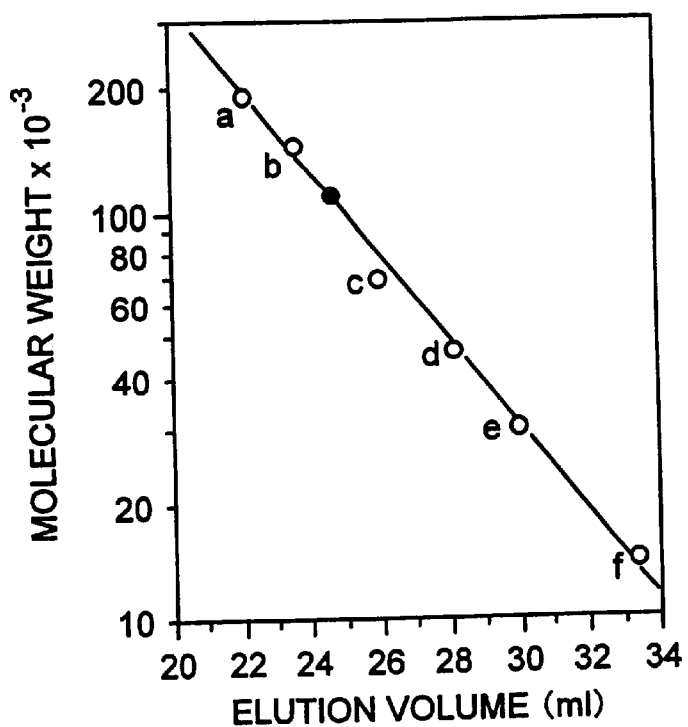
FIG. 1 illustrates the determination of molecular weight of purified Oplophorus luciferase by gel filtration.

According to the present invention, a photoprotein having a molecular weight of 19 kDa is one component of Oplophorus luciferase.

In one embodiment of the invention, the 19 kDa protein having a luminous activity contains an amino acid sequence selected from the group consisting of:

(a) an amino acid sequence for amino acids at positions 28–196 of the amino acid sequence shown in SEQ ID NO: 2; and (b) an amino acid sequence of (a) in which one or several amino acids are deleted, substituted or added.

In another embodiment of the invention, the photoprotein further comprises an amino acid sequence for purification and/or a signal peptide sequence for extracellular secretion or intracellular transport, for example, a signal sequence contained in positions 1–27 of the amino acid sequence shown in SEQ ID NO: 2 or a signal peptide sequence known in the art.

Examples of the signal peptide for the extracellular secretion include eucaryotic secretional signal peptides known in the art (see, e.g., von Heijne, G. Eur. J. Biochem 133 (1983), pp. 17–21) and procaryotic secretional signal peptides known in the art (see, e.g., von Heijne, G. & Abrahmsen, L. FEBS Lett. 244 (1989), pp. 439–446).

Examples of the signal peptide for the intracellular transport include the signal peptides for the transport to mitochondria (Gavel, Y. & von Heijne, G., Protein Engineering 4 (1990), pp. 33–37), for the transport to chloroplast (see, e.g., Gavel, Y. & von Heijne, G., FEBS Lett. 261 (1990), pp.455–458) and for the transport to nuclear (see, e.g., Dingwall, C. & Laskey, R. A., Trends in Biochem. Sci. 16 (1991), pp. 478–481).

According to the invention, a protein having a molecular weight of 35 kDa is another component of Oplophorus luciferase. The 35 kDa protein contains an amino acid sequence selected from the group consisting of:

(a) an amino acid sequence for amino acids at positions 40–359 of the amino acid sequence shown in SEQ ID NO: 4; and (b) an amino acid sequence of (a) in which one or several amino acids are deleted, substituted or added. Said protein further comprises a signal sequence contained in positions 1–39 of the amino acid sequence shown in SEQ ID NO: 4.

Further, the present invention provides a polynucleotide encoding the photoprotein having a molecular weight of 19 kDa. Such polynucleotides include a deoxyribonucleic acid molecule such as cDNA or a genome DNA, a ribonucleic acid molecule such as mRNA and a derivative thereof.

In a preferred embodiment of the invention, the polynucleotide encoding the 19 kDa protein which contains the luminous activity comprises:

(a) a polynucleotide sequence of positions 46–633 of the sequence shown in SEQ ID NO: 1;

(b) a polynucleotide sequence hybridizing to the polynucleotide of (a) under the stringent hybridization condition and encoding a photoprotein; or (c) a polynucleotide sequence complementary to the sequence (a) or (b).

The invention also provides a polynucleotide encoding a protein having a molecular weight of 35 kDa which is one component of Oplophorus luciferase.

In a preferred embodiment of the invention, the polynucleotide comprises:

(a) a polynucleotide sequence of positions 79–1155 of the sequence shown in SEQ ID NO: 3;

(b) a polynucleotide sequence hybridizing to the sequence of (a) under the stringent hybridization condition; or (c) a polynucleotide sequence complementary to the sequence (a) or (b).

In another embodiment of the invention, the foregoing polynucleotide encoding the 19 kDa and/or 35 kDa protein may comprise an additional poly- or oligo-nucleotide encoding a signal peptide known in the art, e.g., the peptide as described in the afore-mentioned literatures.

According to the invention, a method for generating the luminescence comprises reacting the luciferase composed of the 19 kDa and 35 kDa proteins, or the 19 kDa protein with coelenterazine or derivatives thereof as a substrate. The luminescent reaction can occur by the luciferase or the 19 kDa protein as an enzyme, coelenterazine or derivatives thereof as a substrate luciferin and molecular oxygen. The luminescent reaction can be performed at pH of 5.5 to 11, preferably 7.0 to 11. The reaction temperature is in the range of 10° C. to 50° C., preferably 20° C. to 35° C.

According to the invention, a recombinant vector comprises the polynucleotide encoding the 19 kDa protein or the polynucleotide encoding the 35 kDa protein as an insert. In a preferred embodiment of the invention, the recombinant vector is a recombinant expression vector capable of transcribing the polynucleotide of the invention. Such a vector can be prepared by any techniques known in the art.

A vehicle used for the construction of the recombinant vector of the protein of the invention may be any vehicle known in the art that is suitable for in vitro translation system or the expression system using a host cell, for example, microorganism such as *E. coli* and yeast or a cultured animal cell. Such vehicles are commercially available.

Examples of the vehicle for the in vitro translation and the expression in an animal cell include pTargetT vector incorporating the immediate-early enhancer/promoter from Human cytomegalovirus (CMV) containing T7 promoter sequence and multi-cloning site downstream thereto, pSI vector (Promega, Madison, Wis., USA) incorporating SV40 enhancer and SV40 early promoter, pBK-CMV, CMV-Script, pCMV-Tag and pBK-RSV (Stratagene, USA) and the like.

Examples of the vehicle for the expression in *E. coli* include pET expression vector series incorporating T7 promoter (e.g., pET3a, pET27b(+) and pET28a(+); Novagen, Madison, Wis., USA) and the like.

Examples of the vehicle for the expression in yeast include pIC expression vector series incorporating the promoter from alcoholoxydase (e.g., pPIC9K, PIC3.5K; Invitorgen, La Jolla, Calif., USA) and the like.

The present invention further provides a host cell transformed with the recombinant vector. Examples of a host cell include a microorganism, e.g., *E. Coli* and yeast and a cultured animal cell known in the art, e.g., COS7 cell and CHO cell.

According to the present invention, a method for producing the protein of the invention comprises culturing the host cell and then isolating the recombinant protein from cultured media and/or cells, for example, cell extract thereof, and optionally purifying the protein to give a substantially purified form. The isolation of the recombinant protein can be carried out in accordance with the standard technique in the art. The protein can be also isolated from a water-insoluble fraction of the cells by treating one or more solubilizing agents known in the art. Purification of the recombinant protein can be conducted by any procedure known in the art.

In a different embodiment of the present invention, a method for producing the protein comprises subjecting the recombinant expression vector to in vitro translation, isolating the recombinant protein expressed, and optionally purifying the protein to give a substantially purified form. The in vitro translation for producing the protein can be performed by a method known in the art (see, e.g., Spirin, A. S., et. al., Science 242 (1988), pp. 1162–1164; and Patnaik, R. & Swartz, J. R. BioTechniques 24 (1998), pp.862–868). Commercially available in vitro translation kits (e.g., TNT in vitro Transcription-translation kit; Promega) may be used for the in vitro translation.

In another embodiment of the present invention, the method for producing the protein of the invention further comprises renaturing the protein in the presence of a solvent such as one or more polyhydric alcohols for the reactivation of its enzyme activity, and optionally preserving the protein in the solvent. According to the invention, the luciferase and/or the photoprotein can be preserved over a long period of time without decreasing the luminescence activity.

Examples of polyhydric alcohols as a solvent may include, but not limited to, glycerol, polyethylene glycol, polypropylene glycol, dextran, mannitol, sorbitol, inositol, xylitol, sucrose, fructose and glucose. Preferable one is glycerol, polyethylene glycol, or polypropylene glycol, and glycerol is more preferable for preventing the protein from decreasing its enzyme activity. The concentration of one or more polyhydric alcohols is in the range of from 10 to 90% (v/w), preferably from 30 to 90% (v/w), more preferably from 50 to 70% (v/w).

In another embodiment of the present invention, a protein constituting the luciferase and capable of stabilizing the luciferase contains one or more units of leucine-rich repeating sequence consisting of:

(Leu/Ile)-Xaa-Xaa-Leu-Xaa-(Leu/Ile)-Xaa-Xaa-Asn-Xaa-(Leu/Ile)-Xaa-Xaa-Xaa-Pro (SEQ ID NO:39)

wherein each Xaa may be any one of essential amino acids. This leucine-rich repeating structure is found in the amino acid sequence of the 35 kDa protein as shown in FIG. 2. Thus, a protein containing the above repeated sequence may be capable of stabilizing the luciferase as well as the 35 kDa protein.

Further, the invention provides a polyclonal or monoclonal antibody which is arisen against the luciferase of the invention, the 19 kDa or 35 kDa protein, or an immunogenic fragment thereof, and which can specifically bind to the luciferase and/or the protein. Examples of an antigen, which may be used for the-preparation of the antibody according to the present invention, include a protein from a natural source, a recombinant protein, a partially degraded product thereof and a synthetic peptide produced on the basis of the amino acid sequences of the proteins according to the invention. Such synthetic peptides comprise at least 5 contiguous amino acid residues, preferably 10–15 contiguous amino acid residues selected from the sequence consisting of amino acids at positions 28–196 of the sequence shown in SEQ ID NO: 2 and the sequence consisting of amino acids at positions 40–359 of the sequence shown in SEQ ID NO: 4.

The antibody of the present invention can be prepared according to the standard technique in the art (see, e.g., Harlow, E. & Lane, D, in Antibodies-Laboratory manual Cold Spring Harbor Laboratory Press, pp. 53–138 (1988)).

The antibody according to the present invention can be used to detect Oplophorus luciferase or a protein as a component of the luciferase. The antibody can also be used for screening other luciferases or photoproteins which are homologous with the luciferase or the protein of the present invention.

Accordingly, the invention also provides a method for detecting or screening a luciferase or photoprotein using the antibody. The method according to the invention can serve to easily identify a luciferase or a photoprotein derived from systematically related species. In this connection, a novel luciferase or photoprotein identified by the present method may be included within a scope of the present invention.

According to the method of the invention, crude extract of other luminous shrimp or other organisms or their tissues containing a photoprotein is used as a sample and detection and/or screening is carried out in the presence of a protein bound to the antibody of the present invention. The detection techniques may include the immunoblotting and the immuno-chromatography.

The expression cloning (see, e.g., Sambrook, J., Fritsch, E. F., & Maniatis, T., Molecular Cloning—a Laboratory Manual, Second Edition, Cold Spring Harbor Laboratory Press, pp. 12.3–12.44 (1989)) can also be carried out with a gene library (e.g., a cDNA or genomic library) derived from other luminous shrimp or other organisms or their tissues containing a photoprotein using the antibody of the invention to obtain a novel luciferase or photoprotein or a gene thereof.

The invention also provides an oligonucleotide comprising at least 10 contiguous nucleotides selected from a polynucleotide sequence encoding the 19 kDa protein shown in SEQ ID NO: 2 or a complementary sequence thereto.

In a preferred embodiment of the invention, the oligonucleotide may be selected from a polynucleotide sequence shown in SEQ ID NO: 1 or a complementary sequence thereto.

The invention also provides an oligonucleotide comprising at least 10 contiguous nucleotides selected from a polynucleotide sequence encoding the 35 kDa protein shown in SEQ ID NO: 4 or a complementary sequence thereto.

In a preferred embodiment of the invention, this oligonucleotide may be selected from a polynucleotide sequence shown in SEQ ID NO: 3 or a complementary sequence thereto.

The length of the oligonucleotide of the invention is preferably at least 14 nucleotides encoding 5 amino acids, more preferably at least 20 nucleotides encoding 7 amino acids. Further, the oligonucleotide may include a suitable restriction site at its 5' end. The oligonucleotide can be used to detect a polynucleotide molecule such as DNA or RNA encoding the protein which is one component of the luciferase, by the standard technique known in the art, preferably by a polymerase-chain-reaction (PCR) method.

In another embodiment of the invention, a gene library (cDNA or genomic library) derived from other luminous shrimp or other organisms or their tissues containing a photoprotein (enzyme) may be subjected to a suitable cloning, preferably by the PCR method using the oligonucleotide of the invention to isolate a polynucleotide encoding a novel luciferase or a photoprotein.

Thus, the invention also provides a method for detecting and/or screening a gene coding for a luciferase or photoprotein using the oligonucleotide of the invention. Accordingly, a novel gene coding for a novel luciferase or its subunit protein or a novel photoprotein identified by the method of the present invention may be included within a scope of the invention. The method can serve to easily identify a polynucleotide encoding a luciferase or a photoprotein derived from systematically related species, for example, a luciferase having more than 50% homology.

EXAMPLES

The present invention is further illustrated by the following examples. These examples are not to be construed as limiting the scope of the invention.

Example 1

Purification and Identification of the Protein Components of Oplophorus Luciferase The deep-sea luminous shrimp (*Oplophorus gracilirostris*) obtained in the Suruga Bay, Shizuoka, Japan were used as a starting material. A crude extract containing Oplophorus luciferase was prepared in the same manner as disclosed by Shimomura, et al., in Biochemistry 17 (1978) and further purified by chromatography in two steps. The first step was by hydrophobic interaction chromatography on a column of butyl Sepharose 4 Fast Flow (Pharmacia; 0.7 cm×3.5 cm) using 20 mM Tris-HCl, pH 8.5, eluting with decreasing concentrations of ammonium sulfate starting at 1.5 M. The second step was by gel filtration on a column of Superdex 200 Prep (Pharmacia; 1 cm×48 cm) in 20 mM Tris-HCl, pH 8.5, containing 50 mM NaCl. The molecular weight of Oplophorus luciferase was estimated to be about 106 kDa by gel filtration on the same column when compared with the molecular weight markers as follows: (a) amylase (200 kDa); (b) alcohol dehydrogenase (150 kDa); (c) bovine serum albumin (67 kDa); (d) ovalbumin (45 kDa); (e) carbonic anhydrase (29 kDa); and (f) ribonuclease (13.7 kDa). The results are shown in FIG. 1.

SDS-PAGE analysis (12% polyacrylamide gel) of the purified samples gave two major protein bands corresponding to molecular weights of 35 kDa and 19 kDa, respectively. A solution of purified luciferase (25 μg protein in 0.3 ml) dissolved in 0.1% (w/v) SDS was subjected to high performance liquid chromatography (HPLC) on a gel filtration column, TSK 3000SW (Toso; 0.75 cm×30 cm), using 20 mM Tris-HCl, pH 7.7, containing 0.1 M NaCl and 0.1% SDS. The elution profile monitored at 280 nm shows two major components, i.e., 35 kDa and 19 kDa proteins. Thus, native Oplophorus luciferase of about 106 kDa is suggested to be composed of each two, subunits of the 35 kDa and 19 kDa proteins.

Example 2

Determination of an Amino Acid Sequence of Oplophorus Luciferase

The amino acid sequence analysis was carried out using Applied Biosystems model 470A gas phase sequencer according to protocols of the manufacturer. Sample proteins for the sequence analysis were prepared as described below.
(1) The two protein bands of the purified luciferase, the 35 kDa and 19 kDa, separated by SDS-PAGE using 12% polyaclylamide gel were transferred electrophoretically onto a polyvinylidene difuoride membrane (Millipore, Bedford, Mass., USA) at 150 mA for 1 hour. The membranes were then stained and the two bands of the 35 kDa and 19 kDa were subjected to sequence analysis to determine their partial amino acid sequences.

(2) The 35 kDa protein was obtained from the native luciferase (50 μg) by reversed phase HPLC on a 5C4 column (Waters; 0.39 cm×15 cm) by gradient elution with increasing concentrations of acetonitrile (0–80% in 80 min; solvent: acetonitrile/water/0.1% trifuoroacetic acid). Then, the peak fractions were collected by monitoring at 220 nm, concentrated under reduced pressure and subjected to sequence analysis to determine their amino acid sequences. The protein was then digested with lysylendopeptidase (Boehringer; sequencing grade) at a weight ratio of enzyme/substrate of 1:50. The peptide fragments obtained were separated by reversed phase HPLC on a 5C8 column (Vydac; 0.46cm×25 cm) by gradient elution with increasing concentrations of acetonitrile (15–55% in 80 min; solvent: acetonitrile/water/0.1% trifuoroacetic acid). The peak fractions were collected by monitoring at 220 nm and subjected to sequence analysis to determine their amino acid sequences.

The amino acid sequences determined as described above were shown below.

The amino acid sequence of the 19 kDa proteins:
THE N-terminal sequence (SEQ ID NO: 5):
Phe-Thr-Leu-Ala-Asp-Phe-Val-Gly-Asp-Trp-Gln-Gln-Thr-Ala-Gly-Tyr-Asn-Gln-Asp-Gln-Val-Leu-Glu-Gln-Gly-Gly-Leu-Ser The amino acid sequence of the 35 kDa proteins:
The N-terminal sequence (SEQ ID NO: 6):
Ala-Val-Ala-Xaa-Pro-Ala-Ala-Glu-Asp-Ile-Ala-Pro-Xaa-Thr-Xaa-Lys-Val-Gly-Glu-Gly-Asp-Val-Met-Asp-Met-Asp-Xaa-Ser-Lys wherein Xaa represents an undetermined amino acid.

The amino acid sequences of the peptide fragments obtained by digestion with lysylendopeptidase:

SEQ ID NO: 7: Val-Thr-Ser-Asp-Ala-Glu-Leu-Ala-Ser-Ile-Phe-Ser-Lys-Thr-Phe-Pro

SEQ ID NO: 8: Asn-Asp-Leu-Ser-Ser-Phe-Pro-Phe-Glu-Glu-Met-Ser-Gln-Tyr-Thr-Lys

SEQ ID NO: 9: Leu-Val-Leu-Gly-Tyr-Asn-Gly-Leu-Thr-Ser-Leu-Pro-Val-Gly-Ala-Ile

SEQ ID NO: 10: Asn-Leu-Asp-Pro-Ala-Val-Phe-His-Ala-Met-Xaa-Gln wherein Xaa represents an undetermined amino acid.

Example 3

Construction of Oplophorus cDNA Library and Cloning of a Gene Encoding Oplophorus Luciferase Live specimens of *O.gracilirostris* obtained in the Suruga Bay were frozen on dry ice and stored at −80° C. until used. Total RNA was prepared by the guanidine isothiocyanate method (see, e.g., Inouye, S. & Tsuji, F.I., FEBS Lett., 315 (1993), pp. 342–346) followed by precipitation with 2M LiCl. The yield of total RNA from two whole specimens (body size: 40 mm length, 2.8 g wet-weight) was approximately 0.9 mg. Then, poly(A)⁺ RNA (2 μg) was isolated by oligo (dT)-cellulose spun-column (Pharmacia, Piscataway, N.J., USA) and subjected to the synthesis of cDNA with $dT_{12-18}$ primers using a cDNA synthesis kit (Time saver cDNA synthesis kit; Pharmacia) according to Kakizuka, et al. (Essential Developmental Biology, Stern, C. D. ed., IRL Press, Oxford, U.K., pp. 223–232 (1993)). The synthesized cDNAs (20 ng) were ligated with EcoRI/NotI linker. Then, cDNAs were ligated with 1 μg of EcoRI digested/calf intestinal alkaline phosphatase-treated λZapII vector (Strategene, La Jolla, Calif., USA) in a total volume of 5 μl at 4° C. for 16 hours and then packaged in vitro using Gigapack Gold III packaging kit (Stratagene). The titer of the cDNA library was $1.1 \times 10^6$ plaque-forming units.

Example 4

Preparation of Synthesized Oligonucleotide for Probes and PCR Primers

For the isolation of cDNA clone encoding the 19 kDa or 35 kDa protein from the cDNA library, the sequences of the oligonucleotides were designed based on the information of the amino acid sequences determined in Example 2. The oligonucleotides chemically synthesized according to the standard technique were used for the screening or PCR method.

As to an amino acid sequence Ala-Gly-Tyr-Asn-Gln-Asp-Gln (SEQ ID NO: 11) corresponding to the 19 kDa protein, oligonucleotide probe SOL-2: 5'-GCN-GGN-TA-(T/C)-AA(T/C)-CA(A/G)-GA(T/C)-CA-3' (SEQ ID NO: 13) was synthesized. As to an amino acid sequence Gly-Asp-Val-Met-Asp-Met-Asp (SEQ ID NO: 12) corresponding to the 35 kDa protein, the oligonucleotide probe OL-3: 5'-GTN-GT(T/C)-GTN-ATG-GA(T/C)-ATG-TC-3'(SEQ ID NO: 14) was synthesized.

Example 5

Isolation of Clones Encoding the 19 kDa and 35 kDa Proteins of Oplophorus Luciferase The Oplophorus cDNA library obtained in Example 3 was screened by the plaque hybridization technique according to Wallace, R. B., et al. (Nucl. Acids Res., 9 (1981), pp. 879–894 using synthetic oligonucleotide probes, SOL-2 for the 19 kDa protein or OL-3 for the 35 kDa protein. SOL-2 and OL-3 were labeled with [γ-$^{32}$P]ATP (3000 Ci/mmol) at their 5'-end for use as a probe.

Thirty-five thousand independent plaques (per 15 cm LB-plate including 1.2% agalose/1% bactotryptone/0.5% yeast extract/0.5% NaCl, pH 7.2) were lifted onto two membrane filters, then cross-linked with Stratagene UV cross-linker. The filters were prehybridized in 20 ml of the hybridization solution containing 900 mM NaCl/90 mm Tris-HCl (pH 8.0)/6 mM EDTA/0.2% bovine serum albumin/0.2% polyvinyl-pyroridon/0.2% Ficoll/1% SDS/0.05% salmon sperm DNA at 50° C. for 1 hour, and hybridized with the labeled probes for 16 hours. After the hybridization, the filter was washed three times in SSC containing 300 mM NaCl/30 mM sodium citrate at room temperature and subjected to the autoradiography. Resultant positive plaques were picked up and subjected to the second screening, which was carried as described above, and then each single phage clone was isolated. The cDNA inserts were excised as pBluescript phagemids (Stratagene). Resultantly, one positive clone was isolated from 300,006 independent plaques using SOL-2 probe and 9 positive clones were isolated from 70,000 independent plaques using OL-3 probe.

Example 6

Preparation of Recombinant Plasmid Vectors

The recombinant plasmid DNA for each clone obtained in Example 5 was prepared from *Escherichia coli* by the alkaline lysis method. One positive clone from SOL-2 for the 19 kDa protein was designated as pKAZ-412. On the other hand, restriction enzyme analysis of nine positive clones from OL-3 for the 35 kDa provided identical restriction maps and thus the longest clone was designated as pOL-23.

Example 7

Nucleotide Sequence Analysis and Identification of the Luciferase Gene

The nucleotide sequence of each clone was determined by the dye-terminator cycle sequencing method using Applied Biosystems DNA sequencers. The nucleotide sequences of the clones are shown in SEQ ID NOS: 1 and 3, and their deduced amino acid sequences are shown in SEQ ID NOS: 2 and 4.

The 19 kDa protein consists of 196 amino acid residues including a putative signal peptide sequence for secretion, which correspond to the nucleotide sequence of positions 46–633 of the sequence shown in SEQ ID NO: 1. From the results of the N-terminal sequence analysis in Example 2, the mature protein is expected to consist of 169 amino acid residues corresponding to an amino acid sequence of positions 28–196 of the sequence shown in SEQ ID NO: 2 and to have a calculated molecular mass of 18,689.50 and an estimated pI value of 4.70.

The 35 kDa protein consists of 359 amino acid residues including a putative signal peptide sequence for secretion, which correspond to the nucleotide sequence of positions 79–1155 of-the sequence shown in SEQ ID NO: 3. From the results of the N-terminal sequence analysis in Example 2, the mature protein is expected to consist of 328 amino acid residues corresponding to an amino acid sequence of positions 40–359 of the sequence shown in SEQ ID NO: 4 and to have a calculated molecular mass of 34,837.08 and an estimated pI value of 4.61.

The amino acid sequences of the peptide fragments determined in Example 2 were completely identical with the deduced amino acid sequence in SEQ ID NOS: 2 and 4. Therefore, it is confirmed that pKAZ-412 and pOL-23 cloned according to the invention encode the 19 kDa and 35 kDa proteins of Oplophorus luciferase, respectively.

Example 8

Homology Search for the Sequences of Oplophorus Luciferase Shown SEQ ID NOS: 1 to 4

Regarding the nucleotide sequences shown in SEQ ID NOS: 1 and 3 and the amino acid sequences shown in SEQ ID NOS: 2 and 4, their sequence homology was studied by a gene database search with all the database registered for the National Center of Biotechnology Information (NCBI) using computer programs such as FASTA and BLAST. The nucleotide sequences shown in SEQ ID NOS: 1 and 3 were searched for all nucleotide sequences deposited. The amino acid sequences shown in SEQ ID NOS: 2 and 4 were searched for all amino acid sequences deposited and amino acid sequences deduced from the nucleotide sequences deposited. However, the nucleotide sequences shown in SEQ ID NOS: 1 and 3 have no significant homology with any sequence deposited. The amino acid sequences shown in SEQ ID NO: 2 and 4 also have no significant homology with any deposited sequence. Particularly, they have no significant homology with Renilla luciferase (36 kDa; Genebank, M63501), aequorin (21.5 kDa; Genebank, L29571), Renilla luciferin binding protein (20.5 kDa; SWISS-PRO, P05938), Cypridina luciferase (58.5 kDa; Genebank, M25666), firefly luciferase and bacterial luciferase.

The amino acid sequence of the 19 kDa protein shown in SEQ ID NO: 2 has low homology [26% identity (44/169) and 49% similarity (83/169)] to D3-S1 domain (residues 217–392) of *E. coli* amine oxidase (Accession No. pir 140924). The sequence also has low homology [28% identity (13/47): 51% similarity (24/47)] with the amino-terminal region of a fatty acid binding protein (GenBank, L23322), whereas no functional relationship between the 19 kDa protein and these proteins was detected.

As shown in FIG. 2, the amino acid sequence of the 35 kDa protein shown in SEQ ID NO: 4 contains leucine-rich repeating structures consisting of: (Leu/Ile)-Xaa-Xaa-Leu-Xaa-(Leu/Ile)-Xaa-Xaa-Asn-Xaa-(Leu/Ile)-Xa-a-Xaa-Xaa-Pro wherein each Xaa represents any amino acid residue.

Example 9

Figure 3:
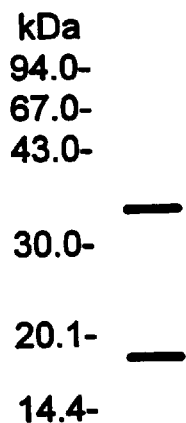
FIG. 3 shows the Western blot analysis of Oplophorus luciferase using the anti-Oplophorus luciferase polyclonal antibody according to the invention.

Preparation of Antibodies Against Oplophorus Luciferase and Western Blot Analysis Purified native Oplophorus luciferase (80 µg) obtained in Example 1 was used to immunize a female New Zealand White rabbit according to the standard technique in the art. The resultant anti-Oplophorus luciferase serum (dilution: 500) was used for Western blot analysis as previously reported (Inouye, S., et al., Anal. Biochem., 201: 114–118 (1992)). The antibody specifically recognized the 19 kDa and 35 kDa proteins (FIG. 3). Thus, using the antibody obtained, it is possible to detect or search the Oplophorus luciferase and other luciferases with the similar primary structure or conformation.

Example 10

Figure 4:
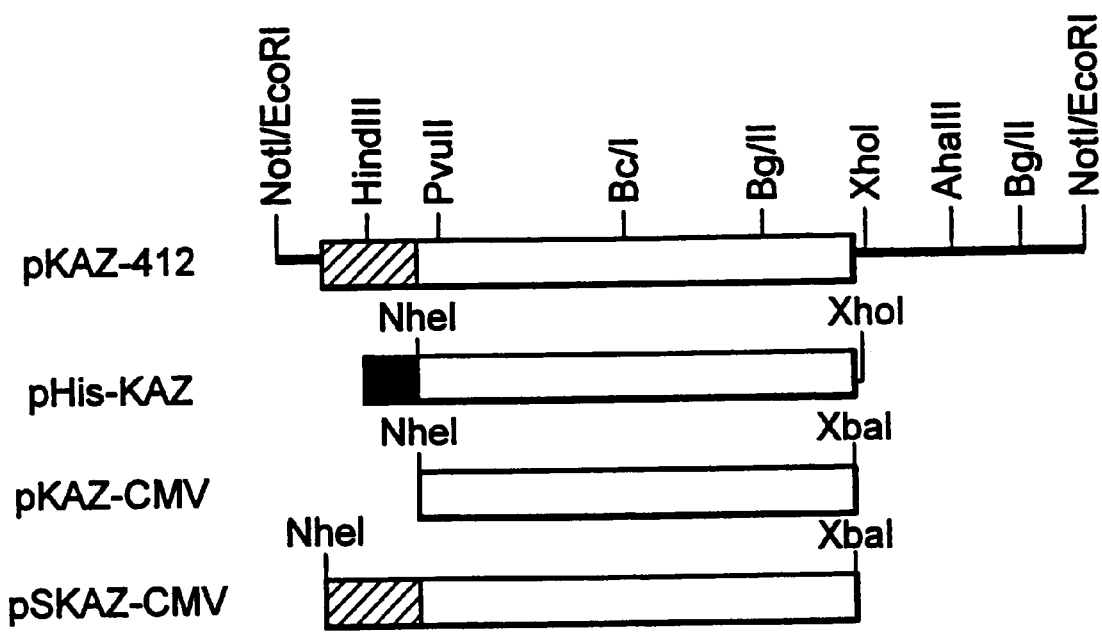
FIG. 4 schematically illustrates the restriction map of the 19 Kda protein and the construction of the expression vector.
Figure 5:
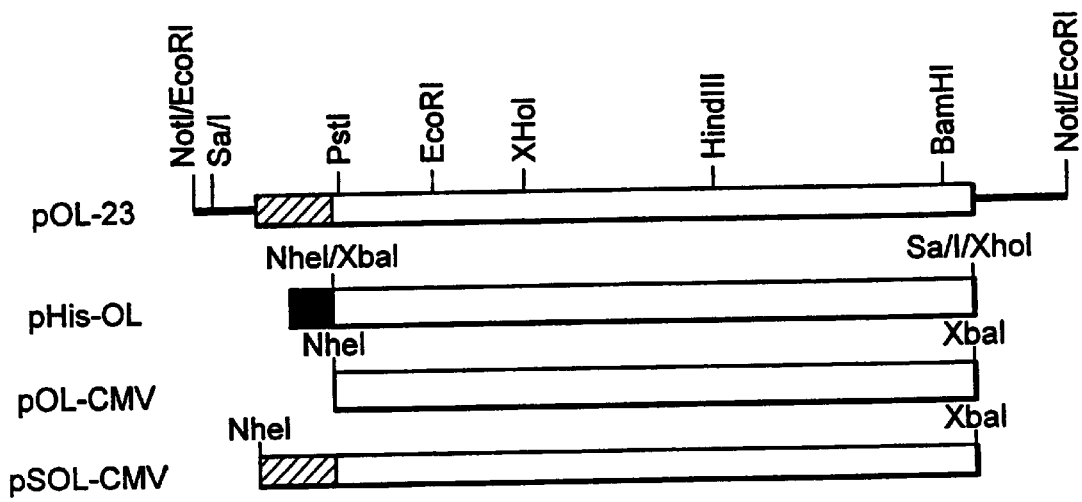
FIG. 5 schematically illustrates the restriction map of the 35 Kda protein and the construction of the expression vector.

Preparation of Plasmid Expressing the Protein Constituting Oplophorus Luciferase The recombinant proteins were expressed in *E. coli* or a cultured cell line by inserting the recombinant vector pKAZ-412 or pOL-23 obtained in Example 6 into the expression vector system. The restriction map of the expression vectors used in this example is shown in FIGS. 4 and 5.

(1) The expression vector for *E. coli* can be constructed by amplifying a DNA fragment encoding either the 19 kDa or 35 kDa protein, i.e., the DNA fragment corresponding to positions 28–196 of an amino acid sequence shown in SEQ ID NO: 2 or positions 40–359 of an amino acid sequence shown in SEQ ID NO: 4 by the polymerase chain reaction (PCR) method and inserting the DNA fragment into a suitable restriction enzyme site of pTrcHis-B (Invitrogen, La Jolla, Calif.) containing a histidine-tag.

More specifically, for the construction of the expression vector for the 19 kDa protein, the desired DNA fragment was amplified by PCR reaction (25 cycles; 1 min at 94° C., 1 min at 50° C., 1 min at 72° C.) with PCR kit (Nippon Gene, Toyama, Japan) using pKAZ-412 as a template and a primer set; KAZ-3. (SEQ ID NO: 15): 5'-CCG GCTAGC-TTT-ACG-TTG-GCA-GAT-TTC-GTT-GGA-3' (NheI site underlined) and T7-BcaBEST (SEQ ID NO: 16): 5'-TAATAC-GACTCACTATAGGG-3', digested with NheI/XhoI and inserted into NheI/XhoI site of pTrcHis-B to provide the expression vector pHis-KAZ.

For the construction of the expression vector for the 35 kDa protein, the desired DNA fragment was amplified by the PCR reaction in the same manner as the above except for using pOL-23 as a template and a primer set; OL-7 (SEQ ID NO: 17): 5'-CCG TCTAGA-GCT-GTT-GCC-TGT-CCT-GCA-GCC-3' (XbaI site underlined) and; OL-8 (SEQ ID NO: 18): 5'-GCC GTCGAC-TTA-TTG-GCA-CAT-TGC-ATG-GAA-3'; SalI site underlined), digested with XbaI/SalI and then inserted into the NheI/XhoI site of pTrcHis-B (Invitrogen) to provide the expression plasmid pHis-OL.

(2) The expression vector for a cultured animal cell can be constructed by amplifying a DNA fragment encoding either the 19 kDa or 35 kDa proteins, i.e., the DNA fragment corresponding to positions 28–196 of an amino acid sequence shown in SEQ ID NO: 2 or positions 40–359 of an amino acid sequence shown in SEQ ID NO: 4 by PCR method, digesting with NheI/XhoI and then inserting the DNA fragment into the NheI/XbaI site of pRL-CMV priviously digested with NheI/XbaI.

More specifically, the expression vectors for the 19 kDa protein, pSKAZ-CMV containing a putative signal sequence for secretion and pKAZ-CMV not containing the signal sequence were constructed in the same manner as described in (1) using the following primers;

KAZ-1 (SEQ ID NO: 19): 5'-CCG GCTAGCCACC-ATG-GCG-TAC-TCC-ACT-CTG-TTC-ATA-3' (NheI site underlined)

KAZ-2 (SEQ ID NO: 20): 5'-CCG GCTAGCCACC-ATG-TTT-ACG-TTG-GCA-GAT-T TC-GTT-GGA-3' (NheI site underlined)

KAZ-5 (SEQ ID NO: 21): 5'-CC GCTCTA-GAA-TTA-GGC-AAG-AAT-GTT-CTC-GCA -AAG-CC-T-3' (XbaI site underlined).

For the construction of PSKAZ-CMV, KAZ-1 and KAZ-5 were used. For the construction of pKAZ-CMV, KAZ-2 and KAZ-5 were used.

The expression vectors for the 35 kDa protein, pSOL-CMV containing a putative signal sequence for secretion and pOL-CMV not containing the signal sequence were constructed in the same manner as described in (1) using the following primers;

OL-4 (SEQ ID NO: 22): 5'-CCG GCTAGCCACC-ATG-GCT-GTC-AAC-TTC-AAG-T TT-3' (NheI site underlined)

OL-5 (SEQ ID NO: 23): 5'-CCG GCTAGCCACC-ATG-GCT-GTT-GCC-TGT-CCT-G CA-GCC-3' (NheI site underlined)

OL-6 (SEQ ID NO: 24): 5'-CCGC TCTAGAA-TTA-TTG-GCA-CAT-TGC-ATG-GAA-3' (XbaI site underlined).

For the construction of pSOL-CMV, OL-4 and OL-6 were used. For the construction of pOL-CMV, OL-5 and OL-6 were used.

Example 11

Expression of the Protein Constituting Oplophorus Luciferase in Cell-free Expression System Using the expression vector, pKAZ-CMV, PSKAZ-CMV, pOL-CMV or pSOL-CMV prepared in Example 10, the 19 kDa or 35' kDa protein constituting Oplophorus luciferase was expressed by means of the in vitro transcription-translation system. As a positive control, pRL-CMV expressing Renilla-luciferase was used. The in vitro transcription-translation system is capable of producing a protein from a recombinant plasmid or mRNA prepared from the plasmid and is particularly useful for the luminescence system with high sensitivity for the detection. In this Example, a commercially available in vitro translation kit (TNT in vitro transcription/translation kit; Promega) was used. A fraction of microsomal membranes capable of cleaving the signal sequence for secretion was also added in order to confirm the existence of the signal sequence in the expressed proteins. The in vitro translation mixture (25 µl in total) containing 0.5 µg of the plasmid DNA, 20 µl of rabbit reticulocyte lysate, 1 µl of 1 mM methionine and 2.5 µl of microsomal membranes was incubated at 30° C. for 90 min and then 1 µl of the mixture was subjected to the measurement of its luminescent activity. A luminescent reaction mixture (100 µl in total) contains 1 µg of coelenterazine in 50 mM Tris-HCl/10 mM EDTA (pH 7.6). The reaction was started by the addition of a test sample and the intensity of the luminescence was measured by the luminometer. Results are shown in Table 2.

TABLE 2

Expression of the protein(s) of Oplophorus Luciferase in Cell-free system

| Expression Plasmid | Expressed protein | Addition of Microsomal membrane | Luminescence activity (rlu) |
|---|---|---|---|
| pRL-CMV | Renilla Luciferase | – | 3253.3 |
| pKAZ-CMV | 19 kDa Protein | – | 1242.0 |
| pSKAZ-CMV | 19 kDa Protein + Signal sequence | – | 3.0 |
| pSKAZ-CMV | 19 kDa Protein + Signal sequence | + | 65.0 |
| pOL-CMV + pKAZ-CMV | 35 kDa + 19 kDa Proteins | – | 581.2 |
| pOL-CMV | 35 kDa Protein | – | <0.001 |
| pSOL-CMV | 35 kDa Protein + Signal sequence | – | <0.001 |
| pSOL-CMV | 35 kDa Protein + Signal sequence | + | <0.001 |
| None | No addition | – | <0.001 |

Significant luminescence activity was found in the 19 kDa protein expressed with pKAZ-CMV. The activity of PSKAZ-CVM, which was lower than that of pKAZ-CMV, was about 20-fold increased by the addition of microsomal membranes. Thus, it was confirmed that the 19 kDa protein had a putative signal sequence for secretion at its N-terminal. Replacing this signall sequence by any other known signal sequence that is efficiently cleaved may solve the problem concerning the signal sequences for secretion.

In addition, the Western blot analysis using the antibody prepared in Example 5 shows the in vitro expression of the 19 kDa or 35 kDa protein.

Example 12

Expression of the Protein Constituting Oplophorus Luciferase in E. coli

E. coli host strain, BL21, was transformed with the expression vectors, pHis-KAZ and pHis-OL constructed in Example 10 and pTrcHis-B as a control plasmid in the standard technique in the art. One hundred microliter of overnight culture was transfered to Luria-Bertani (LB) broth containing 50 µg/ml of ampicillin and cultured for 2 hr at 37° C. Protein production was induced by the addition of isopropyl-β-thio-galactopyranoside (the final concentration: 0.2 mM) at 37° C. in LB broth. After incubation for 3 hours, cells were harvested and then subjected to SDS-PAGE analysis to detect the protein products. As a result, two major bands corresponding to molecular weights of 20 kDa and 36 kDa were observed. The molecular size of these products appeared larger because the proteins further comprises 14 amino acid residues containing 6 histidines for purification with a Nickel-chelated column. In the Western blot analysis, these bands were specifically recognized by both the anti-His monoclonal antibody (Qiagen) and the anti-luciferase antibody obtained in Example 9. These facts mean that the expressed proteins are the 19 kDa and 35 kDa proteins of oplophorus luciferase, which contain the histidine-sequence at the N-terminal.

The protein production was induced by IPTG as described above. The cells were harvested from 1 ml of the culture by centrifugation at 10,000 rpm and then disrupted by sonication in 1 ml of a sonication buffer (30 mM Tris-HCl/10 mM EDTA, pH 7.6). After centrifugation at 10,000 rpm at 4° C., the supernatant was collected and used as the cell extract for the luminescence assay. One μg of coelenterazine or bisdeoxycoelenterazine was added as a substrate into the cell extract and the intensity of the luminescence was measured by the luminometer. The results are shown in Table 3.

TABLE 3

Expression of the protein(s) of Oplophorus Luciferase in *E. coli*

| Strain/Host | Add. of IPTG | Luminescence activity (rlu) | |
|---|---|---|---|
| | | Coelenterazine | Bisdeoxycoelenterazine |
| pHis-KAZ/BL21 | − | 220 | 170 |
| pHis-KAZ/BL21 | + | 14,700 | 12,800 |
| pHis-OL/BL21 | − | 13 | 13 |
| pHis-OL/BL21 | + | 15 | 13 |
| pTrcHis-B/BL21 | − | 10 | 10 |
| pTrcHis-B/BL21 | + | 13 | 12 |

In this example, one relative luminescence unit (rlu) corresponds to about $1.25 \times 10^7$ photons/second. Table 3 shows that the luminescence activity of the strain transformed with pHis-KAZ is approximately 10,000-fold higher than those of pTrcHis-B as a negative control and pHis-OL. Therefore, the above results demonstrate that only the 19 kDa protein out of the 19 kDa and 35 kDa proteins constituting Oplophorus luciferase has the luminescence activity and that the 19 kDa protein can independently generate the luminescence and can utilize both of coelenterazine and bisdeoxy-coelenterazine as a substrate. These facts suggest that the 35 kDa protein in the luciferase is functionally involved not in the substrate specificity but in the stability of the luciferase such as heat-resistance property.

Example 13

Expression of the Protein Constituting Oplophorus Luciferase in Mammalian Cells

Expression of the proteins as a component of Oplophorus luciferase in mammalian cultured cells COS7 was conducted using the expression plasmids pKAZ-CMV, pSKAZ-CMV, pOL-CMV and pSOL-CMV constructed in Example 10 and pRL-CMV expressing Renilla luciferase as a control for the transfection of the host. COS7 cells ($2 \times 10^5$ cells) were grown in a 35 mm well-plate containing 3 ml of Dulbecco's modified Eagle's media (Gibco BRL, Rockville, Md., USA) supplemented with 10% (v/v) heat-inactivated fetal calf serum (Gibco BRL), 100 U/ml penicillin and 100 μg/ml of streptomycin. The cells were cultured at 37° C. for 24 hours and then transfected with 2 μg of each plasmid DNA using FuGENE6 transfection:reagent (Rosche Diagnostics, Mannheim, Germany). After further incubation for 36 hours, cells were separated from cultured media by centrifugation. The separated cells were suspended in 0.5 ml of phosphate-buffered saline, and subjected to repeated freeze-thawing at a temperature between 37° C. and −80° C. to obtain a cell extract. One μg of coelenterazine or bisdeoxy-coelentrazine was added as a substrate into the cell extract and the intensity of the luminescence was measured by the luminometer. The results are shown in Table 4.

TABLE 4

Expression of the protein(s) of Oplophorus Luciferase in COS7 cell

| Expression vector | Luminescence activity (rlu) | | |
|---|---|---|---|
| | in Medium | in Cell extracts | |
| | Coelenterazine | Coelenterazine | Bisdeoxycoelenterazine |
| pRL-CMV | 2.86 | 2,059.5 | 2.61 |
| pKAZ-CMV | 3.62 | 2,273.0 | 2,124.0 |
| pSKAZ-CMV | 1.89 | 297.5 | 217.0 |
| pOL-CMV | 2.45 | <0.001 | <0.001 |
| pSOL-CMV | 2.14 | <0.001 | <0.001 |
| None | 1.92 | <0.001 | <0.001 |

The significant luminescence was observed in the extracts from the cells transfected with plasmids, pKAZ-CMV, PSKAZ-CMV and pRL-CMV as a positive control. For pSKAZ-CMV, a low secretional efficiency into the medium is consistent with the results in Example 11. The luminescent intensity from pKAZ-CMV is equivalent to that from pRL-CMV which is commercially available. This suggests that the gene coding for the 19 kDa protein derived from Oplophorus luciferase may be a good candidate for use as a new reporter protein in mammalian cell systems Example 14

Isolation and Renaturation of the Insoluble Protein Expressed in *E. coli*

*E. coli* cells constructed in Example 12 which contain the expression vector pHis-KAZ and express the 19 kDa protein were disrupted by the sonication in 20 ml of a buffer comprising 20 mM Tris-HCl, pH 7.5. After centrifugation (12,000×g, 20 minutes), the precipitated fraction was subjected to the solubilization by treating with 20 ml of 20 mM Tris-HCl, pH 7.5 containing 8 M urea and then centrifuged (12,000×g, 20 minutes) to afford a soluble fraction. SDS-PAGE analysis of this fraction shows approximately 95% yield of the 19 kDa protein (data not shown). Subsequently, the soluble fraction was subjected to the nickel-chelated column chromatography and the desired protein was eluted by the linear gradient of imidazole from 0 to 0.3 M to give approximately 95% purity.

The resultant protein has no luminescence activity at this state. Consequently, the protein was subjected to the renaturation step by treating with glycerol (the final concentration: from 0 to 90% (v/w)) as a solvent at 25° C. for 30 minutes to afford the 19 kDa protein renatured. As described above, the intensity of the luminescence was measured by the luminometer. Results are shown in Table 5.

TABLE 5

| Conc. of glycerol (%, v/w) | Luminescence Activity (rlu) |
|---|---|
| 0 | 83 (1.0) |
| 10 | 147 (1.8) |
| 20 | 375 (4.5) |
| 30 | 1,258 (15.2) |
| 40 | 1,818 (24.9) |
| 50 | 3,822 (46.0) |
| 60 | 4,860 (58.6) |
| 70 | 4,462 (53.8) |

TABLE 5-continued

| Conc. of glycerol (%, v/w) | Luminescence Activity (rlu) |
|---|---|
| 80 | 2,842 (34.2) |
| 90 | 2,536 (30.6) |

As shown in the above table, the 19 kDa protein solubilized by the buffer containing a high concentration of urea could be renatured by treating with glycerol. Particularly, glycerol concentration at 50% to 70% could significantly renature the luminescence activity of the protein.

Subsequently, the 19 kDa protein renatured was subjected to the preservation test, which comprises preserving the protein in the absence or presence of 50% (v/w) or 70% (v/w) glycerol at 4° C. for 30 days and then measuring its luminescence activity as mentioned above. The activity of the protein significantly decreased in the absence of glycerol, whereas in the presence of glycerol, the luminescence activity was maintained without decreasing. These results shown in Table 6.

TABLE 6

| Concentration of glycerol (%, v/w) | Preserving temperature (° C.) | Luminescence activity after preservation (rlu) | |
|---|---|---|---|
| | | 0 day | 30 days |
| 0 | 4 | 102 | 23 |
| 50 | 4 | 3,840 | 3,734 |

INDUSTRIAL APPLICABILITY

The present invention elucidates that the luciferase derived from the deep-sea shrimp, *Oplophorus gracilirostris*, is composed of the 19 kDa and 35 kDa proteins. Isolation of the 19 kDa and 35 kDa proteins from the *Oplophorus gracilirostris* and cloning of the genes encoding them can be achieved according to the invention. The recombinant vectors, the host cell such as a cultured animal cell or a microorganism transformed with the recombinant vector provided by the invention are used to produce the luciferase or the proteins of the invention in a large amount.

The luciferase or the 19 kDa protein can be utilized for various methods for the measurement or analysis as a reporter.

The antibody and oligonucleotide of the invention can be utilized for detecting the presence of a luciferase or the proteins constituting the enzyme and for cloning a gene encoding other luciferases. More specifically, they may be used for identification of a novel luciferase or photoprotein from systematically related species.

What is claimed is:

1. An isolated protein comprising residues 28–196 of SEQ ID NO: 2.

2. The isolated protein of claim 1 that further comprises a peptide sequence for purification.

3. An isolated protein comprising residues 40–359 of SEQ ID NO:4.

4. The isolated protein of claim 3 that further comprises a peptide sequence for purification.

5. The isolated protein of claim 1 that is a recombinantly-produced protein.

6. The isolated protein of claim 1 that is produced in a mammalian cell.

7. An isolated protein comprising a fragment of the isolated protein of claim 1 wherein said fragment has a luciferase activity.

8. A composition comprising the isolated protein of claim 1.

9. The isolated protein of claim 1 that further comprises a signal peptide sequence.

10. The isolated protein of claim 3 that is a recombinantly-produced protein.

11. The isolated protein of claim 3 that is produced in a mammalian cell.

12. A composition comprising the isolated protein of claim 3.

13. The isolated protein of claim 3 that further comprises a signal peptide sequence.

14. A bioassay comprising contacting the isolated protein of claim 1 with a luminescent substrate comprising coelenterazine or a derivative thereof under conditions suitable for the generation of a detectable signal.

15. The bioassay of claim 14, wherein said luminescent substrate comprises coelenterazine or bisdeoxycoelenterazine.

* * * * *